(12) United States Patent
Wakabayashi et al.

(10) Patent No.: US 7,892,175 B2
(45) Date of Patent: Feb. 22, 2011

(54) CAPACITIVE ULTRASONIC PROBE DEVICE

(75) Inventors: Katsuhiro Wakabayashi, Hachioji (JP); Hideo Adachi, Iruma (JP); Yukihiko Sawada, Tokorozawa (JP); Takuya Imahashi, Kawasaki (JP); Masayoshi Omura, Saitama (JP); Etsuko Omura, legal representative, Saitama (JP); Akiko Mizunuma, Hachioji (JP); Shuji Otani, Oume (JP); Miyuki Murakami, Hino (JP); Kiyoshi Nemoto, Hino (JP); Kozaburo Suzuki, Hachioji (JP); Naomi Shimoda, Fukushima (JP)

(73) Assignee: Olympus Corporation, Tokyo (JP)

( * ) Notice: Subject to any disclaimer, the term of this patent is extended or adjusted under 35 U.S.C. 154(b) by 745 days.

(21) Appl. No.: 11/636,677

(22) Filed: Dec. 8, 2006

(65) Prior Publication Data
US 2007/0167814 A1 Jul. 19, 2007

Related U.S. Application Data

(63) Continuation of application No. PCT/JP2005/010592, filed on Jun. 9, 2005.

(30) Foreign Application Priority Data

Jun. 10, 2004 (JP) ............................. 2004-172970
Jun. 17, 2004 (JP) ............................. 2004-180191

(51) Int. Cl.
*A61B 8/00* (2006.01)
(52) U.S. Cl. ...................... 600/437; 600/459; 600/462; 600/463; 600/466
(58) Field of Classification Search ................ 600/437, 600/459, 462, 463, 466
See application file for complete search history.

(56) References Cited

U.S. PATENT DOCUMENTS 5,188,106 A * 2/1993 Nappholz et al. ............. 607/24
5,951,478 A 9/1999 Hwang et al.
6,248,074 B1 * 6/2001 Ohno et al. .................. 600/463
6,499,348 B1 12/2002 Mamayek (Continued)

FOREIGN PATENT DOCUMENTS

JP 01-269080 10/1989

(Continued)

OTHER PUBLICATIONS

Wong, K.A., et al., "Curved Micromachined Ultrasonic Transducers", IEEE Ultrasonics Symposium, 2003, pp. 572-576, vol. 1.

(Continued)

*Primary Examiner*—Brian Casler
*Assistant Examiner*—Baisakhi Roy
(74) *Attorney, Agent, or Firm*—Scully, Scott, Murphy & Presser, PC

(57) ABSTRACT

Within the tip portion of a cylindrical shaped sheath a capacitive ultrasonic transducer which is an array type two-dimensionally arrayed on the outer surface of the cylindrical face is disposed. Capacitive ultrasonic transducer units employ m capacitive ultrasonic transducer elements arrayed in the longitudinal direction of the cylindrical face as a division unit, thereby providing an arrangement wherein the respective capacitive ultrasonic transducer units are readily disposed in the circumferential direction, whereby radial scanning or the like can be performed within a body cavity.

44 Claims, 21 Drawing Sheets

U.S. PATENT DOCUMENTS

| | | |
|---|---|---|
| 6,558,330 B1 | 5/2003 | Ayter et al. |
| 6,705,996 B2 * | 3/2004 | Kawagishi et al. .......... 600/458 |
| 7,507,205 B2 * | 3/2009 | Borovsky et al. .......... 600/466 |
| 2001/0051766 A1 * | 12/2001 | Gazdzinski ................ 600/309 |
| 2002/0087083 A1 | 7/2002 | Nix et al. |

FOREIGN PATENT DOCUMENTS

| | | |
|---|---|---|
| JP | 2-34155 | 2/1990 |
| JP | 3-280939 | 12/1991 |
| JP | 05-184574 | 7/1993 |
| JP | 5-269126 | 10/1993 |
| JP | 8-56949 | 3/1996 |
| JP | 09-065477 | 3/1997 |
| JP | 09-154844 | 6/1997 |
| JP | 9-307987 | 11/1997 |
| JP | 11-151245 | 6/1999 |
| JP | 11-266002 | 9/1999 |
| JP | 2002-159494 | 6/2002 |
| JP | 2004-503312 | 2/2004 |
| JP | 2004-503313 | 2/2004 |
| JP | 2004-154572 | 6/2004 |
| WO | WO 94/17734 | 8/1994 |
| WO | PCT/EP2001/006479 | 6/2001 |
| WO | PCT/EP2001/006868 | 6/2001 |

OTHER PUBLICATIONS

Oralkan, O., et al,. "Volumetric Imaging Using 2D Capacitive Micromachined Ultrasonic Transducer Arrays (CMUTs): Initial Results:", IEEE Ultrasonics Symposium, 2002, pp. 1083-1086, vol. 2.

Demirci, U., et al., "Capacitive Micromachined Ultrasonic Transducer Arrays for Medical Imaging: Experimental Results", IEEE Ultrasonics Symposium, 2001, pp. 957-960, vol. 2.

Daft, C., et al., "Elevation Beam Profile Control with Bias Polarity Patterns Applied to Microfabricated Ultrasound Transducers", IEEE Ultrasonics Symposium, 2003, pp. 1578-1581, vol. 2.

Knight, J.G., et al., Capacitive Micromachined Ultrasonic Transducers for Forward Looking Intravascular Arrays, IEEE Ultrasonics Symposium, 2002, pp. 1079-1082, vol. 2.

Pua, E.C. et al., "Real-time cylindrical curvilinear 3-D ultrasound imaging", Ultrasonic Imaging (2003), vol. 25, No. 3, pp. 137-149.

* cited by examiner

FOCUSING POINT

FOCUSING POINT

ETCHING

ACOUSTIC MATCHING LAYER FORMATION

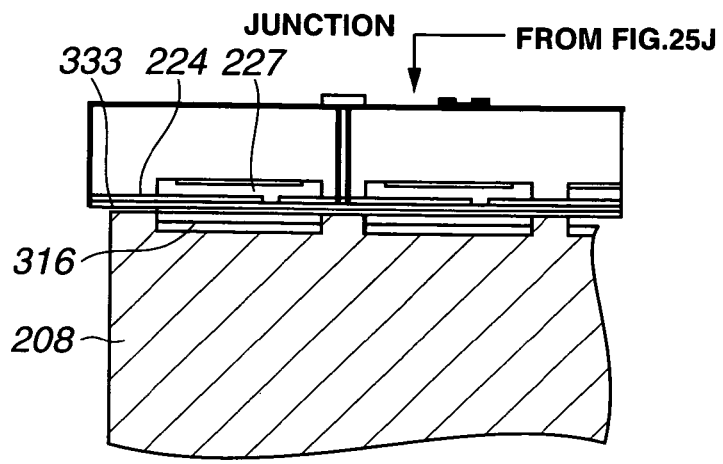
FIG. 25C
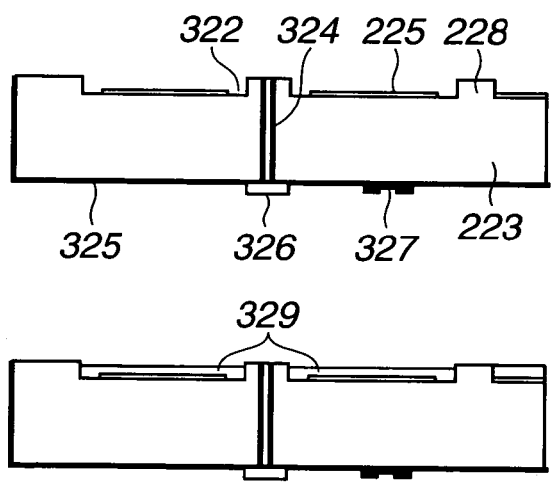
FIG. 25D
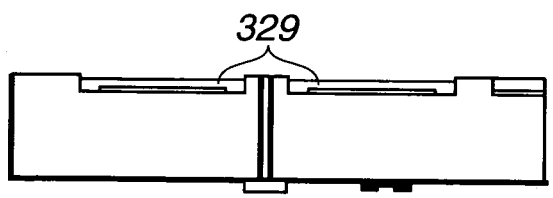
FIG. 25E
FIG. 25F
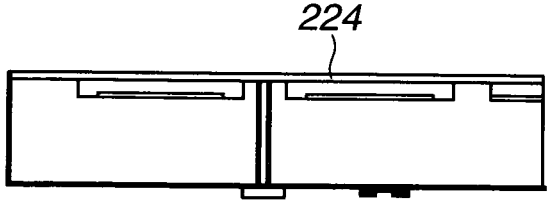
FIG. 25G
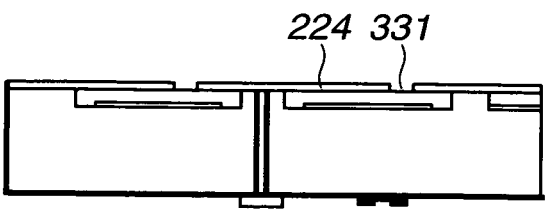
FIG. 25H
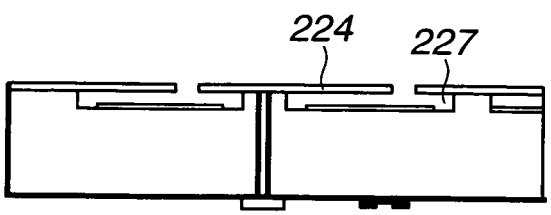

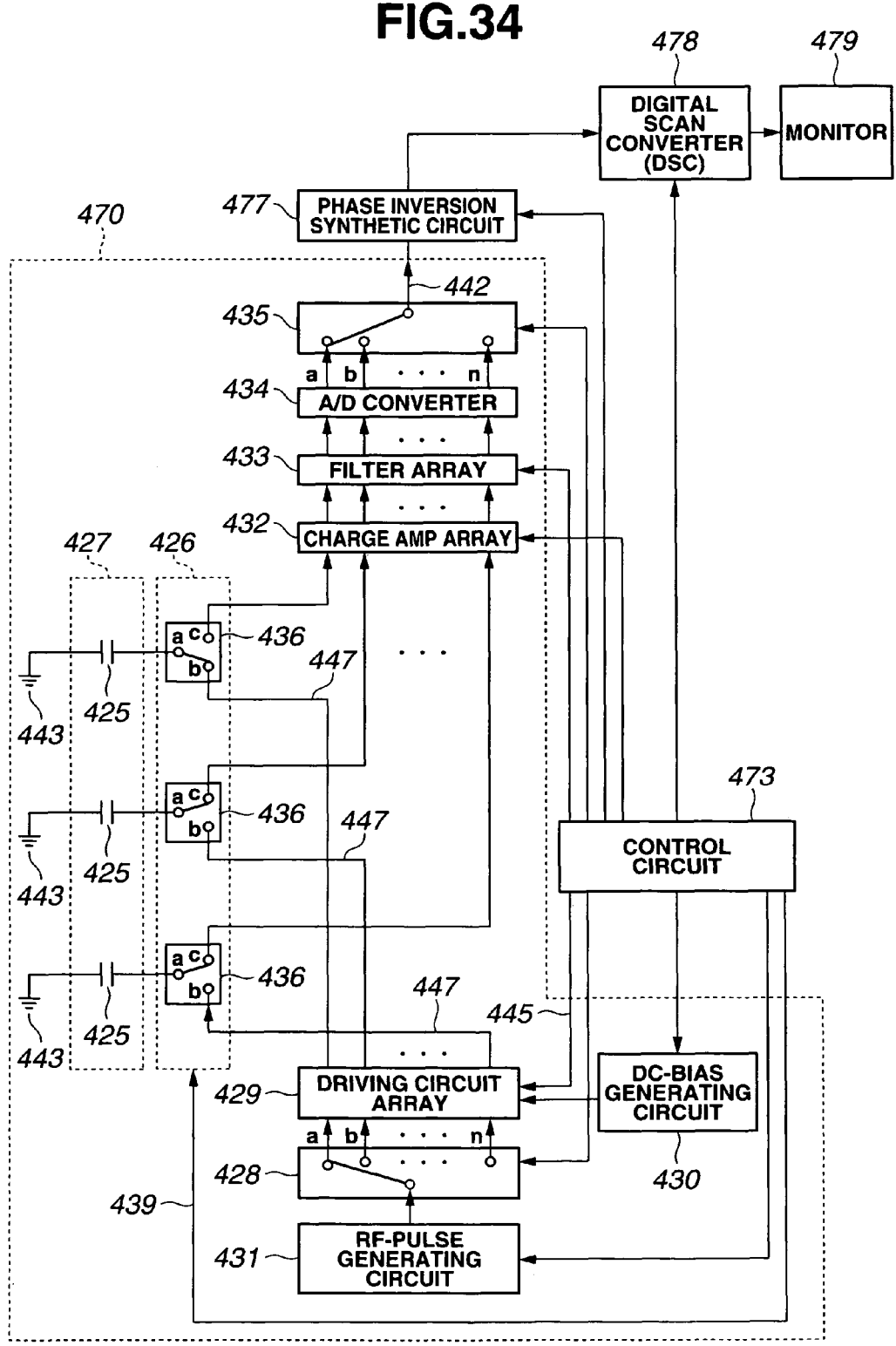

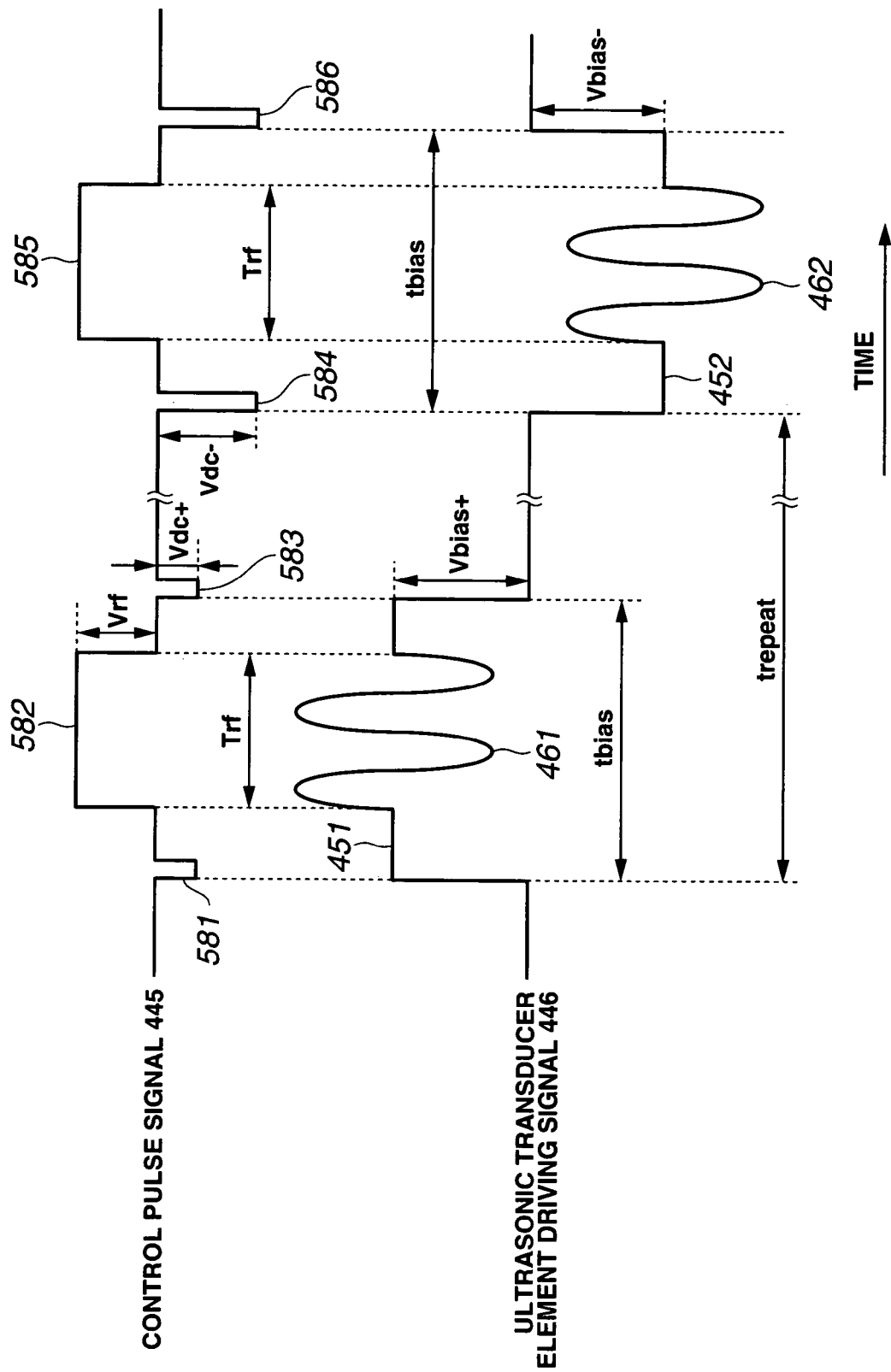

CAPACITIVE ULTRASONIC PROBE DEVICE

CROSS REFERENCE TO RELATED APPLICATION

This application is a continuation application of PCT/JP2005/010592 filed on Jun. 9, 2005 and claims benefit of Japanese Applications No. 2004-172970 filed in Japan on Jun. 10, 2004 and No. 2004-180191 filed in Japan on Jun. 17, 2004, the entire contents of each of which are incorporated herein by their reference.

BACKGROUND OF THE INVENTION

1. Field of the Invention

The present invention relates to a capacitive ultrasonic probe device to be inserted into a body cavity and used for ultrasonic diagnosis.

2. Description of the Related Art

In recent years, ultrasonic probe devices have been widely employed for acoustic diagnosis. Also, these ultrasonic probe devices are usually employed with piezoelectric elements taking advantage of a piezoelectric phenomenon, but nowadays, capacitive ultrasonic probe devices employing a capacitive micromachined ultrasonic transducer (c-MUT) have been proposed.

On the other hand, in recent years, harmonic imaging diagnosis employing high-frequency signals is becoming standard diagnostic modality since a distinct diagnostic image can be obtained, which cannot be obtained with the conventional B mode diagnosis.

The harmonic imaging diagnostic method can be classified into (1) a tissue harmonic imaging method wherein a harmonic wave superimposed upon the fundamental ultrasonic wave in response to influence of nonlinearity of organism tissue at the time of an ultrasonic wave propagating within a body is separated using various types of methods, and an image is formed by employing this signal, and (2) a contrast harmonic imaging method wherein a contrast medium bubble is injected into a body, a harmonic wave which occurs at the time of the bubble being ruptured by irradiation of a transmitting ultrasonic wave is received, the harmonic wave superimposed upon the fundamental ultrasonic wave is separated by various types of methods, and an image is formed by employing this signal.

It has been understood that both of those excel in S/N, which cannot be obtained by conventional B mode tomography, and can obtain diagnostic images with suitable resolution. Both of those have contributed in improvement in medical diagnostic precision.

As an example of the ultrasonic transducers employed for conventional external harmonic imaging diagnostic devices, two-way ultrasonic transducers which can be used for fundamental wave transmission and harmonic wave reception have been employed. Note that an arrangement may be made wherein the echo of an ultrasonic pulse reflected from organism tissue is received at an ultrasonic transducer provided separately from an ultrasonic transducer for transmission.

It is necessary to effectively remove fundamental wave components relating to deterioration of harmonic images since the signal level of a harmonic wave signal is extremely small as compared to the fundamental wave. Therefore, a known harmonic wave component extraction technique (particularly, a second harmonic wave component extraction technique) has been employed.

As described above, as for an ultrasonic transducer, a capacitive ultrasonic transducer obtained by processing a silicon semiconductor substrate using silicon micromachine technology has been proposed, in addition to conventional piezoelectric type ultrasonic transducers.

Capacitive ultrasonic transducers have been disclosed in PCT Japanese Translation Patent Publication No. 2004-503312, and PCT Japanese Translation Patent Publication No. 2004-503313 as conventional examples. These Publications have disclosed capacitive ultrasonic probe devices which aim at external use.

Note that there is a capacitive micromachined ultrasonic transducer configured by layering ultrasonic transducers (c-MUT), such as disclosed in U.S. Pat. No. 6,558,330.

In order to employ the harmonic imaging technology, it is necessary to obtain an ultrasonic transducer including broadband properties, and the capacitive ultrasonic transducers are appropriate for harmonic imaging diagnosis due to the broadband properties thereof.

SUMMARY OF THE INVENTION

A capacitive ultrasonic probe device according to the present invention is characterized to have a configuration wherein an ultrasonic transducer unit is formed with multiple capacitive micromachined ultrasonic transducer (c-MUT) elements in increments of driving, which are formed by disposing multiple capacitive ultrasonic transducer cells using a common electrode along a generally cylindrical shaped outer side face provided at the tip side of an insertion portion capable of being inserted into a body cavity, being arrayed in the direction in parallel with the center axis of the generally cylindrical shape as division increments, and the multiple ultrasonic transducer units are arrayed along the outer circumference of the generally cylindrical shape.

Also, the above configuration is characterized in that the multiple ultrasonic transducer units are joined to a flexible circuit substrate formed in a generally cylindrical shape.

According to the above configuration, the ultrasonic transducer units are formed on the flexible circuit substrate, thereby providing a configuration wherein the ultrasonic transducer units are readily disposed on the generally cylindrical outer side face orthogonal to the longitudinal direction thereof along with the flexible circuit substrate to facilitate use within a body cavity.

According to the above configuration, a capacitive ultrasonic probe device for insertion into a body cavity having a cylindrical shape which facilitates use within a body cavity is realized, and also radial scanning or the like can be performed in a high sensitivity state by arraying the ultrasonic transducer elements in increments of driving formed by the multiple capacitive ultrasonic transducer cells, and further arraying the multiple ultrasonic transducer units along the outer circumference of the cylinder.

A capacitive ultrasonic probe device according to the present invention is a capacitive ultrasonic probe device for inserting an ultrasonic probe into a body cavity, and performing ultrasonic diagnosis within a body by rotating and scanning an ultrasonic beam around the insertion axis, and is characterized to comprise: an ultrasonic transducer disposed and configured such that the ultrasonic probe emits an ultrasonic wave in the insertion axis direction; and an ultrasonic propagation medium including angular components for reflecting an ultrasonic wave emitted and propagated from the ultrasonic transducer in a predetermined angular direction as to the insertion axis.

The ultrasonic transducer has a ring shape, and the ultrasonic propagation medium has a cylindrical shape of which the wall thickness is great, which are disposed and bonded such that both inside diameter circles are concentrically situated.

The ultrasonic transducer is a piezoelectric transducer or capacitive ultrasonic transducer, which is made up of a ring-shaped flat-plate transducer, includes means for performing control so as to transmit or receive an ultrasonic wave with a capacitive ultrasonic transducer element made up of multiple capacitive ultrasonic transducer cells disposed radially as a unit, or means for performing control so as to transmit or receive an ultrasonic wave with the piezoelectric transducer being divided in the same direction to make up an array-type transducer configuration, and with the piezoelectric transducer element as a unit.

Description will be made below in detail regarding the case of employing a capacitive ultrasonic transducer, but the case of employing a piezoelectric transducer is generally the same regarding vibration control.

The capacitive ultrasonic transducer cells are made up of a hollow portion formed on the silicon substrate, a membrane formed within the hollow portion so as to divide the hollow portion, a first electrode mounted on the membrane, a second membrane disposed so as to fill in the hollow portion, and a second electrode formed on the second membrane.

The ultrasonic propagation medium includes a fluid acoustic binding medium on the outer side face in the vicinity where an ultrasonic wave is emitted, and also includes an acoustic matching layer made up of at least one layer for subjecting the fluid acoustic binding medium and the ultrasonic propagation medium to acoustic matching on the outer side face in the vicinity where an ultrasonic wave is entered.

The ultrasonic propagation medium includes an acoustic lens on the outer side face in the vicinity where an ultrasonic wave is emitted.

With such a configuration, radial scanning can be realized, for example, by an arrangement wherein an ultrasonic wave is entered in a cylindrical rod of which end portions are subjected to conical processing in the insertion axis direction from the ring-shaped flat-plate transducer, reflected at the conical processed face in the right-angled direction, the elements arrayed in the circumferential direction of the ring-shaped flat-plate transducer are sequentially driven and controlled. As for the ultrasonic transducer, either of a piezoelectric type or capacitive type may be employed. The conical processed face is a convex curved face as viewed from the ultrasonic incident side, so that the ultrasonic beam reflected thereat is converted into a fan beam. Accordingly, an acoustic focal point can be shifted remotely to improve invasion depth as compared with the conventional probe employing a sheath having the same dimensions and material, and an acoustic binding agent.

On the other hand, with regard to the acoustic matching between the cylindrical rod and the capacitive transducer, the configuration of the capacitive transducer cells is assumed as a configuration wherein a cavity is divided at an intermediate membrane film, the ultrasonic wave which is a longitudinal wave due to bending vibration of the membrane is cast upon the cylindrical rod bonding face through the acoustic matching film. Also, an acoustic matching layer is formed on the cylindrical rod outer side surface to suppress interface reflection.

The elements are arrayed in the diameter direction of the ring-shaped transducer, whereby electronic scanning can be performed in the insertion axis direction.

Note that an optical fiber is inserted into the hollow portion of the cylindrical rod, whereby light irradiation and optical image detection can be performed.

The capacitive ultrasonic transducer can be readily subjected to processing and assembly without the transducer being subjected to curved deformation processing, which is different from a method for manufacturing an ordinary radial scan-type transducer. Further, a pulser portion and a charge amp are provided in the vicinity of the transducer by an Si semiconductor process, which can convert a signal into low impedance, and transmit the signal.

The above configuration can realize a capacitive ultrasonic probe device which can scan an ultrasonic beam in the insertion axis direction, effectively realize acoustic matching with an organism, readily perform processing and assembly, use the capacitive ultrasonic transducer to reduce the effective value of an application voltage within a body cavity, have high sensitivity and high invasion depth, and be used for harmonic imaging diagnosis.

BRIEF DESCRIPTION OF THE DRAWINGS

FIG. 25C is a cross-sectional view describing the manufacturing process at the rod side of the manufacturing method of the capacitive ultrasonic transducer in the ultrasonic probe tip portion.

FIG. 25D is a cross-sectional view describing the manufacturing process at the transducer side of the manufacturing method of the capacitive ultrasonic transducer in the ultrasonic probe tip portion.

FIG. 25E is a cross-sectional view describing the manufacturing process at the transducer side of the manufacturing method of the capacitive ultrasonic transducer in the ultrasonic probe tip portion.

FIG. 25F is a cross-sectional view describing the manufacturing process at the transducer side of the manufacturing method of the capacitive ultrasonic transducer in the ultrasonic probe tip portion.

FIG. 25G is a cross-sectional view describing the manufacturing process at the transducer side of the manufacturing method of the capacitive ultrasonic transducer in the ultrasonic probe tip portion.

FIG. 25H is a cross-sectional view describing the manufacturing process at the transducer side of the manufacturing method of the capacitive ultrasonic transducer in the ultrasonic probe tip portion.

FIG. 34 is a block diagram of a capacitive ultrasonic probe device configured with a two-way capacitive ultrasonic transducer array.

FIG. 35 is a diagram illustrating waveform examples of a control pulse signal and an ultrasonic transducer element drive pulse signal, which describes the operation of the arrayed ultrasonic transducer in FIG. 34.

DETAILED DESCRIPTION OF THE PREFERRED EMBODIMENT(S)

Embodiments of the present invention will be described below with reference to the drawings.

First Embodiment

Figure 1:
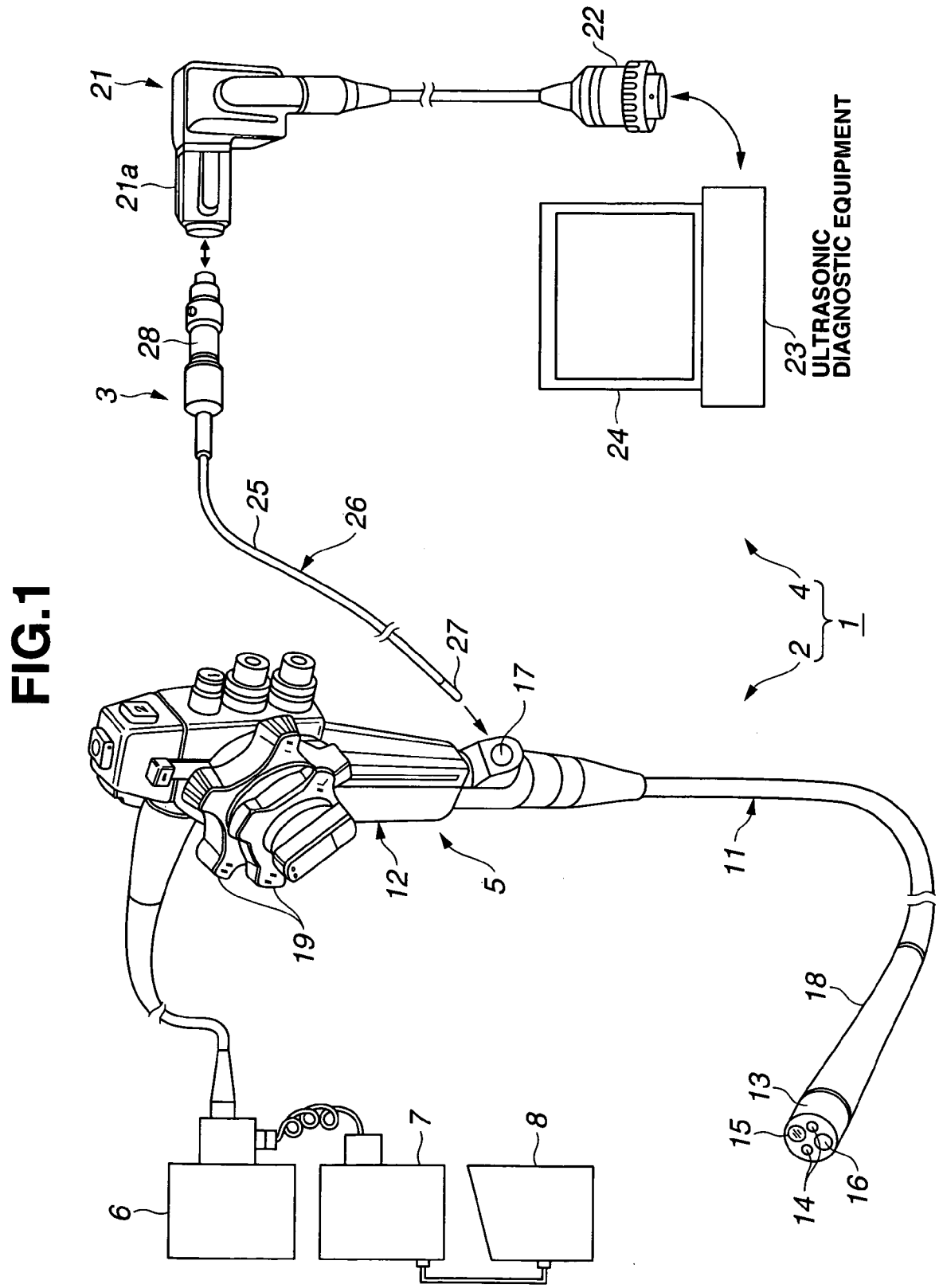
FIG. 1 is an overall configuration diagram of an endoscope ultrasonic system including a capacitive ultrasonic probe device according to a first embodiment of the present invention.
Figure 2:
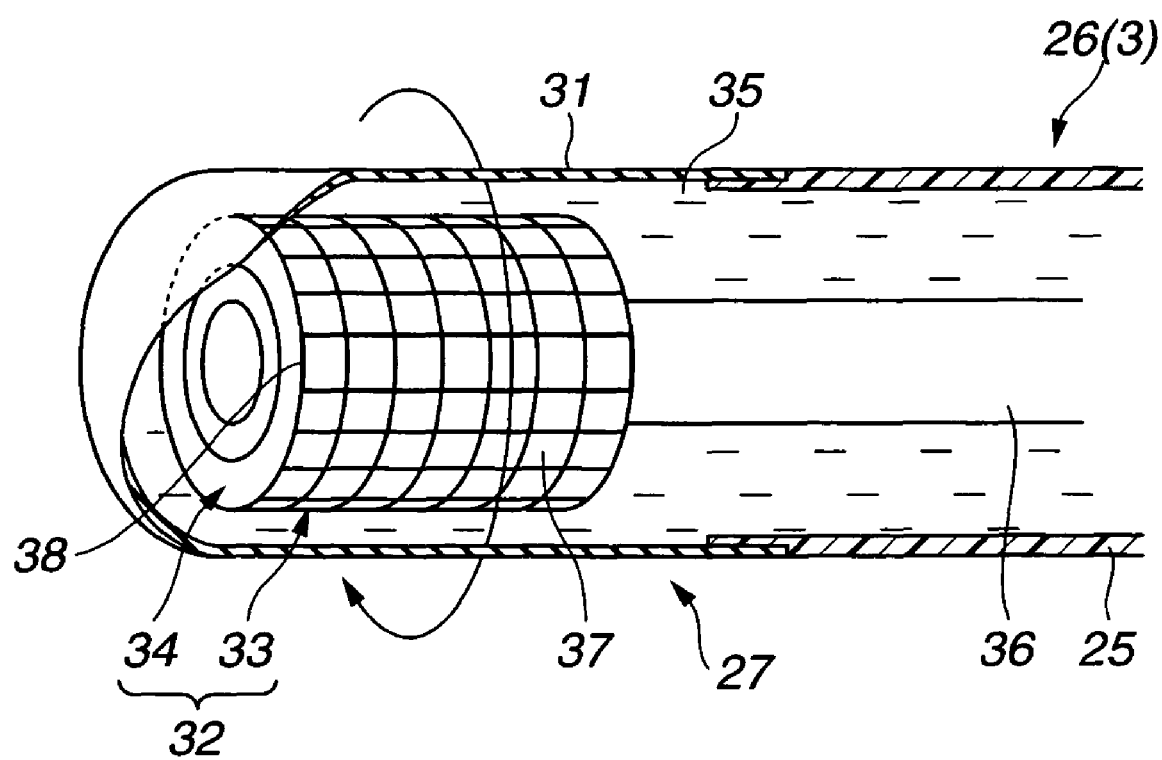
FIG. 2 is a perspective view illustrating a partial cutaway of the configuration of the tip side of the capacitive ultrasonic probe device according to the first embodiment of the present invention.
Figure 3:
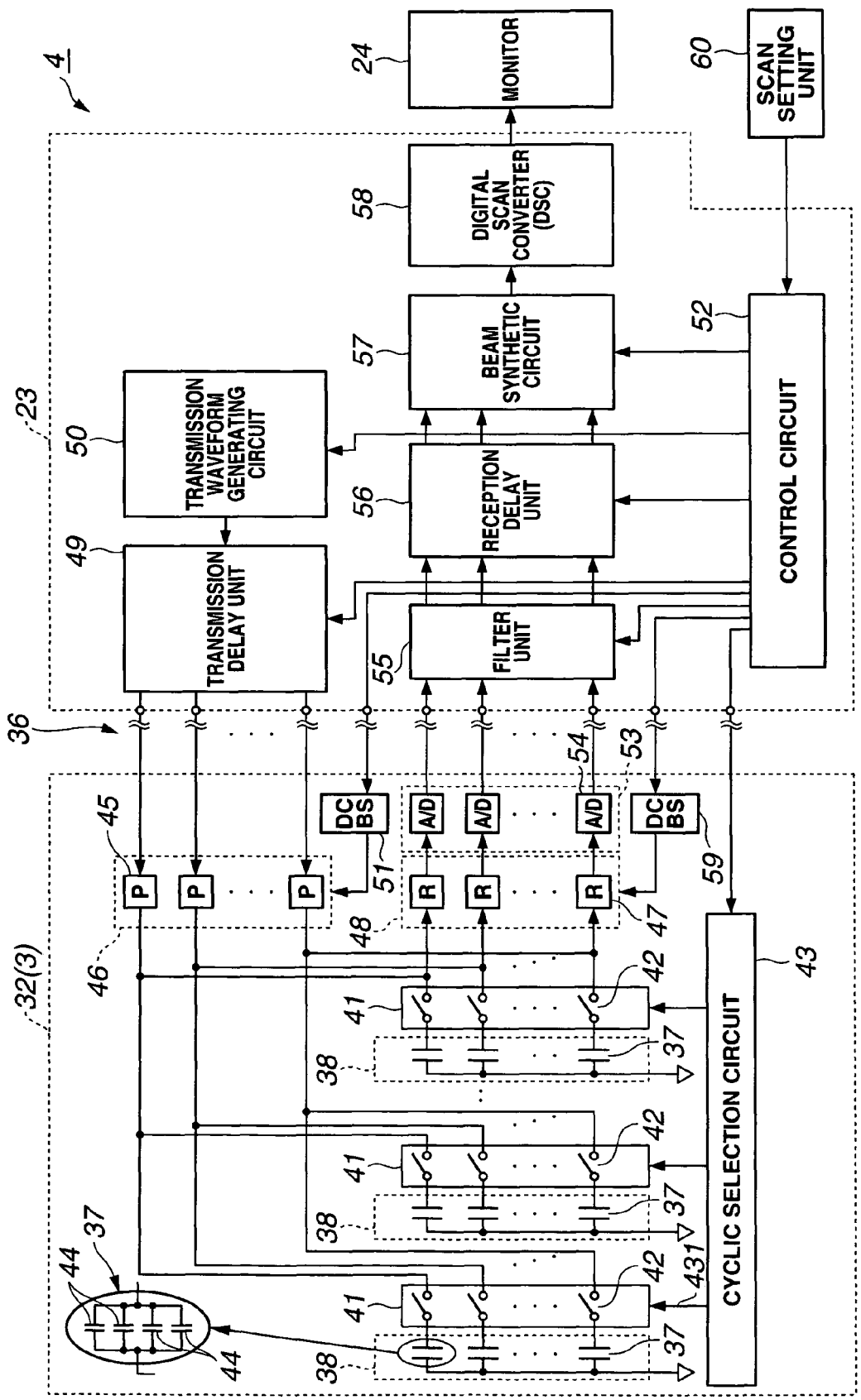
FIG. 3 is a block diagram illustrating the overall configuration of the electric system of an ultrasonic diagnosis device.
Figure 4:
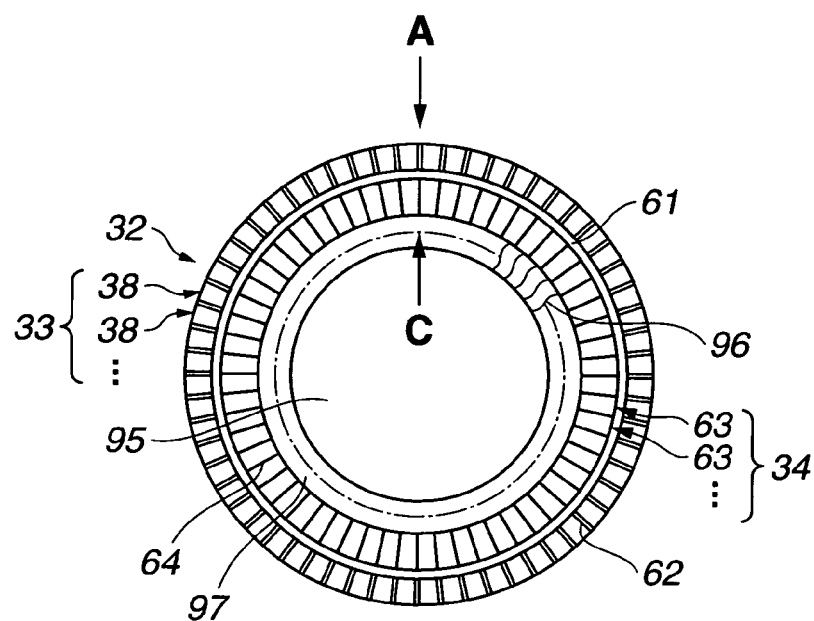
FIG. 4 is a diagram illustrating the cross-sectional configuration of the cylindrical shaped ultrasonic transducer and transducer control circuit block in FIG. 2.
Figure 5:
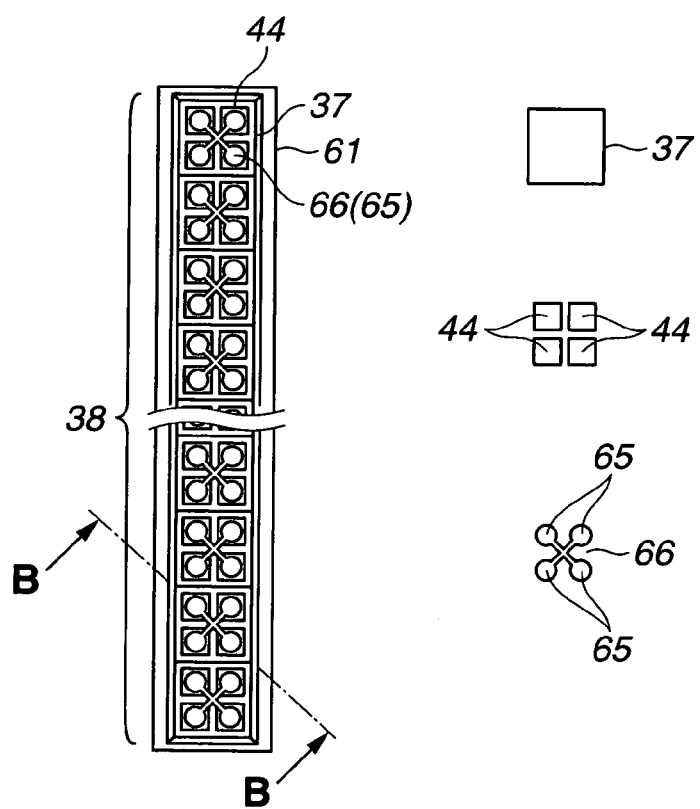
FIG. 5 is a diagram illustrating the configuration of the capacitive ultrasonic transducer unit as viewed from the arrow A direction in FIG. 4.
Figure 6:
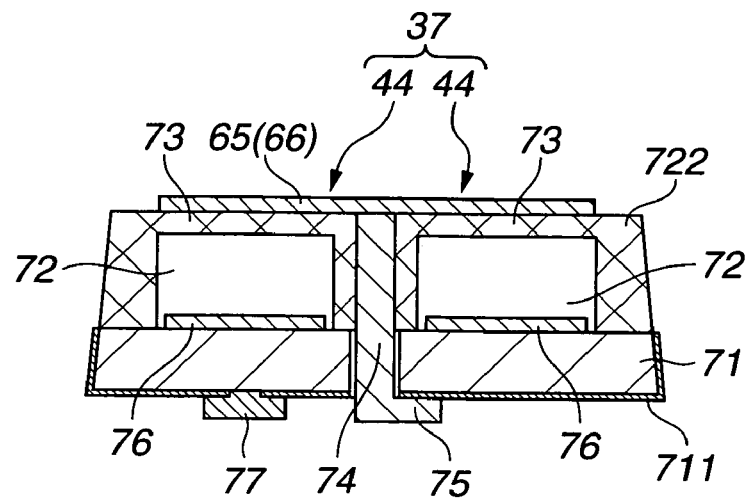
FIG. 6 is a cross-sectional view illustrating the configuration of the capacitive ultrasonic transducer element with the B-B-line cross-section in FIG. 5.

FIG. 1 through FIG. 11 relate to a first embodiment of the present invention, FIG. 1 illustrates the overall configuration of an endoscope ultrasonic system including a first embodiment of the present invention, FIG. 2 illustrates the configuration of the tip side of a capacitive ultrasonic probe device according to the present embodiment, FIG. 3 illustrates the overall configuration of the electric system of an ultrasonic diagnosis device, FIG. 4 illustrates the cross-sectional configuration of the cylindrical shaped ultrasonic transducer and transducer control circuit block in FIG. 2, FIG. 5 illustrates the configuration of the capacitive ultrasonic transducer unit as viewed from the arrow A direction in FIG. 4, and FIG. 6 illustrates the configuration of the capacitive ultrasonic transducer element with the B-B-line cross-section in FIG. 5.

Figure 7:
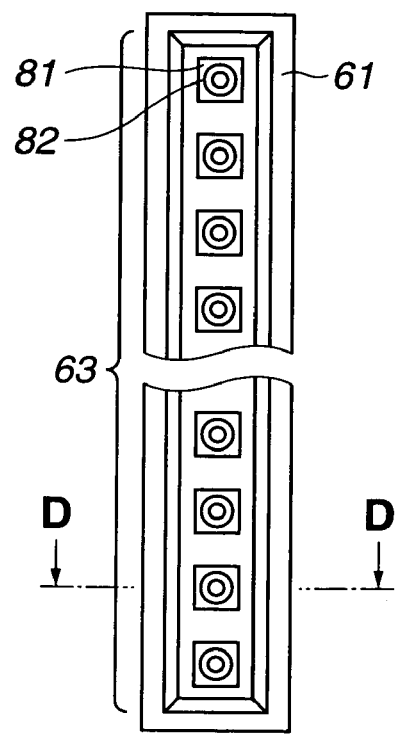
FIG. 7 is a diagram illustrating the configuration of the transducer control circuit unit as viewed from the arrow C direction in FIG. 4.
Figure 8:
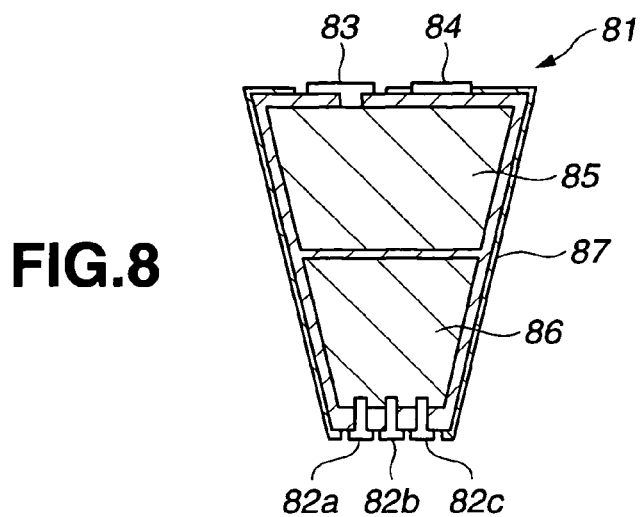
FIG. 8 is a cross-sectional view illustrating the configuration of the transducer control circuit element with the D-D-line cross-section in FIG. 7.
Figure 9A:
FIG. 9A is a diagram illustrating the procedure of the manufacturing process of the ultrasonic transducer and transducer control circuit block.
Figure 9B:
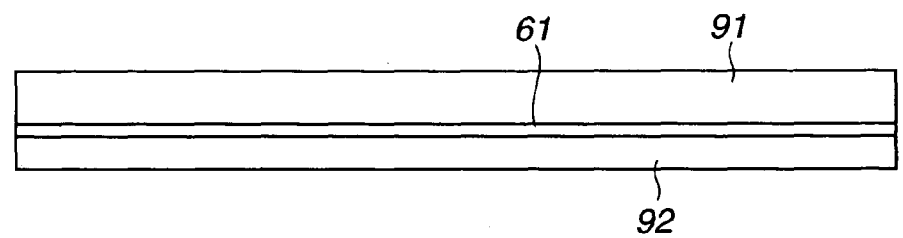
FIG. 9B is a diagram illustrating the procedure of the manufacturing process of the ultrasonic transducer and transducer control circuit block.
Figure 9C:
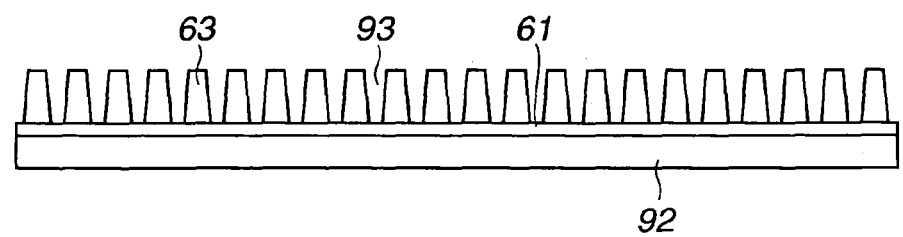
FIG. 9C is a diagram illustrating the procedure of the manufacturing process of the ultrasonic transducer and transducer control circuit block.
Figure 9D:
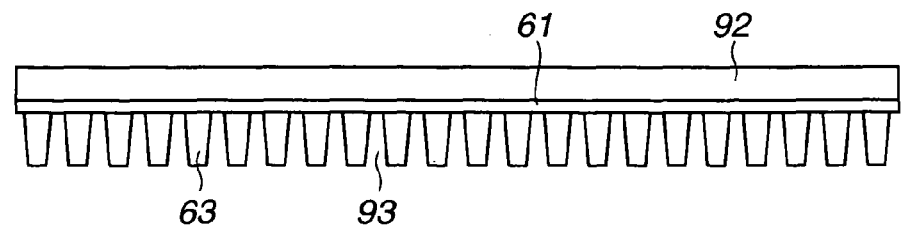
FIG. 9D is a diagram illustrating the procedure of the manufacturing process of the ultrasonic transducer and transducer control circuit block.
Figure 9E:
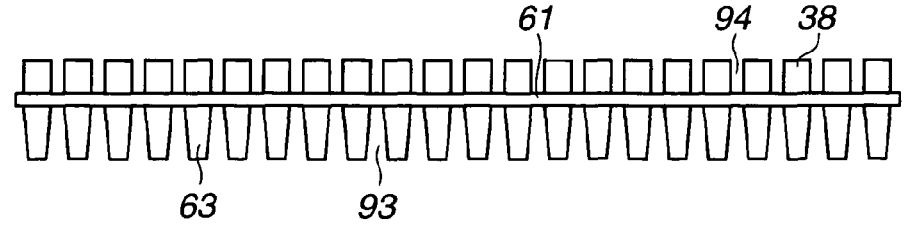
FIG. 9E is a diagram illustrating the procedure of the manufacturing process of the ultrasonic transducer and transducer control circuit block.
Figure 9F:
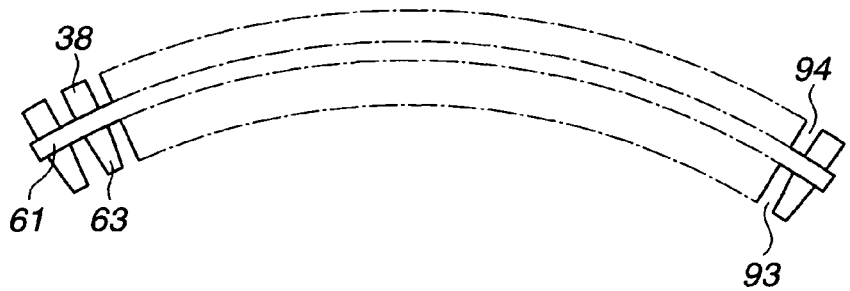
FIG. 9F is a diagram illustrating the procedure of the manufacturing process of the ultrasonic transducer and transducer control circuit block.
Figure 9G:
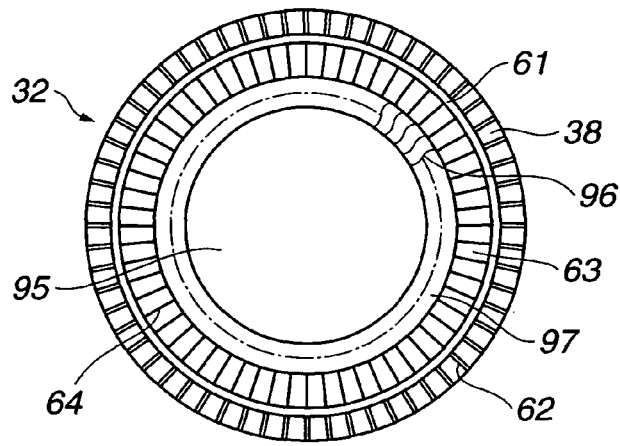
FIG. 9G is a diagram illustrating the procedure of the manufacturing process of the ultrasonic transducer and transducer control circuit block.
Figure 10A:
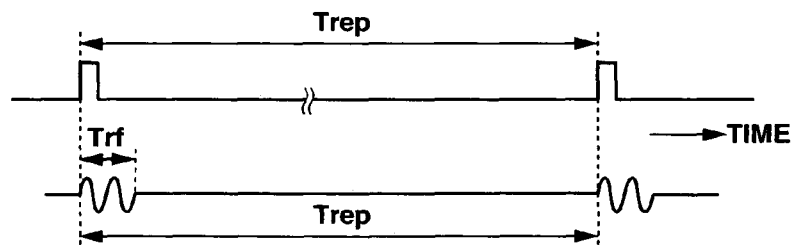
FIG. 10A is an explanatory diagram of ultrasonic driving.
Figure 10B:
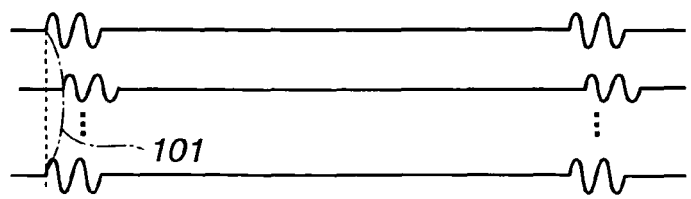
FIG. 10B is an explanatory diagram of ultrasonic driving.
Figure 10C:
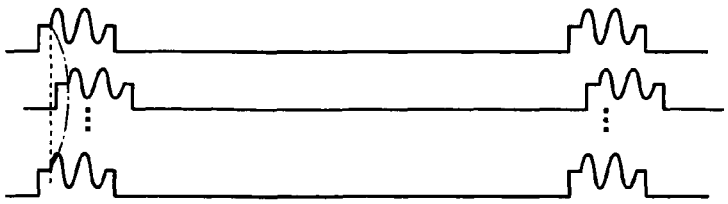
FIG. 10C is an explanatory diagram of ultrasonic driving.
Figure 10D:
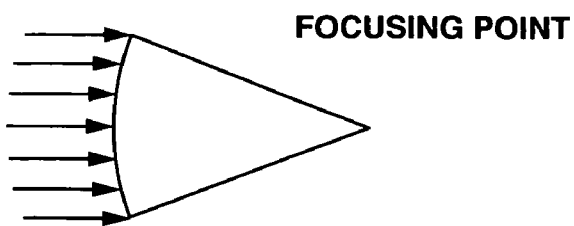
FIG. 10D is an explanatory diagram of ultrasonic driving.
Figure 10E:
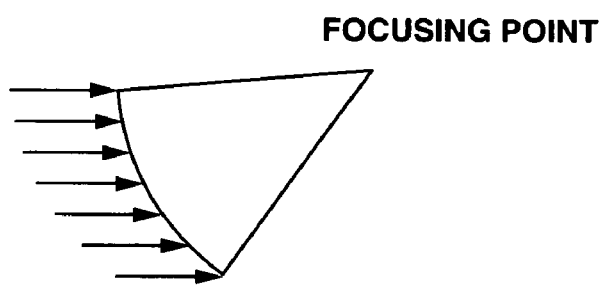
FIG. 10E is an explanatory diagram of ultrasonic driving.
Figure 11:
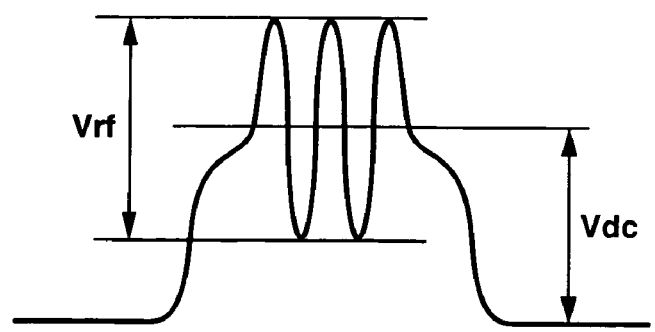
FIG. 11 is a diagram illustrating the waveform of a ultrasonic driving signal.

FIG. 7 illustrates the configuration of the transducer control circuit unit as viewed from the arrow C direction in FIG. 4, FIG. 8 illustrates the configuration of the transducer control circuit element with the D-D-line cross-section in FIG. 7, FIG. 9A through FIG. 9G illustrate the procedure of the manufacturing process of the ultrasonic transducer and transducer control circuit block, FIG. 10A through FIG. 10E illustrate the explanatory diagrams of ultrasonic driving, and FIG. 11 illustrates the waveform of an ultrasonic driving signal.

The endoscope and ultrasonic system 1 illustrated in FIG. 1 comprises an endoscope device 2 for performing endoscopy, a capacitive ultrasonic probe device for insertion into a body cavity (hereafter, abbreviated as capacitive ultrasonic probe device) 3 according to the present embodiment, and an ultrasonic diagnostic device 4 for performing ultrasonic diagnosis.

The endoscope device 2 comprises an endoscope 5, which is inserted into a body cavity, for optically observing, a light source device 6 for supplying illumination light to an unshown light guide inserted into this endoscope 5, a video processor (or camera control unit) 7 for subjecting an image capturing device built in the endoscope 5 to signal processing, and an endoscope monitor 8 for displaying the endoscope image image-captured by the image capturing device in response to the picture signal to be output from this video processor 7 being input.

This endoscope 5 comprises a slender insertion portion 11 to be inserted into a body cavity, and the rear end of the insertion portion 11 is provided with an operating portion 12.

A tip portion 13 of the insertion portion 11 is provided with an illumination window 14 emitting illumination light, and an observation window 15 to which an objective lens is attached for forming an optical image of a subject such as an affected portion within a body cavity illuminated.

The tip portion 13 is provided with a channel exit 16, and this channel exit 16 is communicated with a treatment-tool insertion slot 17 near the base of the insertion portion 11 by an unshown internal channel.

An arrangement is made wherein the capacitive ultrasonic probe device 3 according to the present embodiment is inserted from the treatment-tool insertion slot 17, and thus the tip side of the capacitive ultrasonic probe device 3 is passed through the channel and protruded from the channel exit 16, and is used in a state of being in contact with a subject such as an affected portion or the like, whereby ultrasonic diagnostic images can be obtained.

Note that a bending portion 18 is provided adjacently with the tip portion 13 of the insertion portion 11, and the bending portion 18 can be bent in a desired direction by the bending operating knob 19 of the operating portion 12 being operated. On the other hand, the ultrasonic diagnostic device 4 comprises the capacitive ultrasonic probe device 3 according to the present embodiment, a relay cable portion 21 to be detachably connected to the end of this capacitive ultrasonic probe device 3, an ultrasonic diagnostic equipment 23 to be detachably connected with a connector 22 provided at the end of the relay cable portion 21, and an ultrasonic monitor 24 for displaying an ultrasonic tomogram generated from the ultrasonic echo signal obtained from the capacitive ultrasonic probe device 3 in response to the picture signal to be output from the ultrasonic diagnostic equipment 23 being input.

With the capacitive ultrasonic probe device 3 according to the present embodiment, an insertion portion 26 is formed by being covered by a slender sheath 25 having flexibility, and this insertion portion 26 is configured so as to be inserted into the channel of the endoscope 5.

The tip of the insertion portion 26 is provided with an ultrasonic probe head portion 27 such as illustrated in FIG. 2. Also, the end of the insertion portion 26 is provided with a joint portion 28, which is configured so as to be detachably connected to the joint portion 21a of the relay cable portion 21.

As illustrated in FIG. 2, the tip of the cylindrical shaped sheathe 25 is provided with a cylindrical shaped sheath tip member 31 of which tip side is blocked, and side face portion has high properties in ultrasonic transmittance, and is also rich in deformability such as expansion and contraction and the like such as a balloon, thereby forming the housing of the ultrasonic probe head portion 27.

The sheath tip member 31 stores a columnar or cylindrical ultrasonic transducer and transducer control circuit block 32 therein.

The cylindrical outer circumferential face of the ultrasonic transducer and transducer control circuit block 32 is provided with an array-type capacitive ultrasonic transducer 33, and also the inner circumferential side thereof is provided with a transducer control circuit unit 34.

Also, the circumference of the ultrasonic transducer and transducer control circuit block 32 within the sheath tip member 31 is filled with an acoustic propagation medium 35 for propagating an ultrasonic wave.

Also, the rear end side of the ultrasonic transducer and transducer control circuit block 32 is connected with one end of a cable 36 made up of signal lines such as multiple coaxial lines or the like, and this cable 36 is inserted into the sheath 25, and further connected to the ultrasonic diagnostic equipment 23 via an unshown cable within the relay cable portion 21.

With the array-type capacitive ultrasonic transducer 33, m capacitive ultrasonic transducer elements 37 which are driving increments are arrayed in the axial direction of the cylindrical face, and k elements 37 are arrayed in the circumferential direction of the cylindrical face, thereby forming a two-dimensional array-type capacitive ultrasonic transducer.

With the present embodiment, as described later, a capacitive ultrasonic transducer unit 38 wherein the m capacitive ultrasonic transducer elements 37 are arrayed in the axial direction of the cylindrical face is formed, thereby providing a configuration facilitating two-dimensional array of the capacitive ultrasonic transducer elements 37 on the cylindrical face.

That is to say, the array-type capacitive ultrasonic transducer two-dimensionally arrayed in a flat-plate shape cannot be readily disposed in a cylindrical shape as it is, but it is arranged so as to be readily disposed in a cylindrical shape by being divided into units in the axial direction of the cylindrical face. In this case, in a state in which the array-type capacitive ultrasonic transducer is mounted on the flexible substrate, and also connected to the flexible printed circuit substrate, the respective units are divided, whereby the array-type capacitive ultrasonic transducer can be formed in a cylindrical shape along with the flexible printed circuit substrate.

Upon representing this state using the capacitive ultrasonic transducer units 38, the array-type capacitive ultrasonic transducer 33 two-dimensionally arrayed in a cylindrical shape is formed by the k capacitive ultrasonic transducer units 38 being arrayed in the circumferential direction of the cylindrical face.

Subsequently, the k capacitive ultrasonic transducer units 38 arrayed in the circumferential direction of the cylindrical face are sequentially driven by a driving signal, whereby an ultrasonic beam is transmitted in the direction perpendicular to the face of the driven capacitive ultrasonic transducer unit 38, and consequently, radial scanning can be performed such as illustrated with the arrow in FIG. 2. Also, sector scanning can be performed by performing beamformer which is different from the case of performing radial scanning.

The overall configuration of the electric system of the ultrasonic diagnostic device 4 including the configuration of the ultrasonic transducer and transducer control circuit block 32 will be described with reference to FIG. 3 before describing the three-dimensional configuration of the ultrasonic transducer and transducer control circuit block 32.

As illustrated in FIG. 3, the ultrasonic diagnostic device 4 principally comprises the ultrasonic transducer and transducer control circuit block 32, and the ultrasonic diagnostic equipment 23 to be connected by the cable 36. With the ultrasonic transducer and transducer control circuit block 32, the above respective capacitive ultrasonic transducer units 38 are connected to transducer element selection units 41, respectively. That is to say, the respective capacitive ultrasonic transducer elements 37 making up the respective capacitive ultrasonic transducer units 38 are serially connected to transducer element selection switches 42 making up the transducer element selection units 41, respectively.

Also, the respective transducer element selection units 41 are connected to a cyclic selection circuit 43 making up the ultrasonic transducer and transducer control circuit block 32, all of the transducer element selection switches 42 belonging to the respective transducer element selection units 41 are configured so as to be simultaneously turned on/off by the on/off selection signal 43a from the cyclic selection circuit 43. Thus, radial scanning can be performed.

Note that as enlarged and illustrated with the ellipse in FIG. 3, the respective capacitive ultrasonic transducer elements 37 are made up of multiple capacitive ultrasonic transducer cells 44 sharing electrodes. In the case of FIG. 3, the respective capacitive ultrasonic transducer elements 37 are made up of the four capacitive ultrasonic transducer cells 44.

Thus, the respective capacitive ultrasonic transducer elements 37 are made up of the multiple capacitive ultrasonic transducer cells 44, thereby preventing the amount of displacement from being restricted in the event of the respective capacitive ultrasonic transducer elements 37 made up of the single capacitive ultrasonic transducer cell.

That is to say, the respective capacitive ultrasonic transducer elements 37 are configured so as to be sectioned into small increments, whereby the capacitive ultrasonic transducer elements 37 can be effectively used with a high frequency that can increase resolution. Also, the m capacitive ultrasonic transducer elements 37 are driven with a phase difference for each of the capacitive ultrasonic transducer units 38, whereby the ultrasonic beam to be transmitted to the organism side can be focused, or sector scanning can be performed in the insertion axis direction.

Note that with the respective capacitive ultrasonic transducer elements 37, the ultrasonic emission face side is shared by a ground electrode and grounded, and the electrode at the other signal input side is connected to the transducer element selection switch 42, and an RF driving signal is applied thereto.

The respective capacitive ultrasonic transducer units 38 are each connected to a pulser unit 46 made up of m pulsers 45, and a receiver unit 48 made up of m receivers 47 via the serially connected transducer element selection units 41.

That is to say, the respective capacitive ultrasonic transducer elements 37 are connected to the output ends of the pulsers 45 for generating a large amplitude RF driving signal from a small amplitude RF signal and to the input ends of the receivers 47 for amplifying the echo signal, via the transducer selection switches 42, respectively. Also, the input ends of the pulsers 45 are connected to a transmission waveform generating circuit 50 via the signal lines making up the cable 36, and via a transmission delay unit 49 within the ultrasonic diagnostic equipment 23.

Subsequently, the transmission RF signal generated by the transmission waveform generating circuit 50 is amplified with the pulser unit 46 by the transmission delay unit 49 in the event of radial scanning for example such that the closer to the central side in the m transmission delay circuits the greater the transmission RF signal is delayed, following which the signal is applied to the m capacitive ultrasonic transducer elements 37 for example of the capacitive ultrasonic transducer units 38 which are turned on by the cyclic selection circuit 43 in a state of being delayed by the above delayed phase contrast.

Also, a low-voltage DC bias voltage control signal is input to the pulser unit 46 in a pulse state from a DC bias voltage generating control circuit (abbreviated as DCBS in FIG. 3) 51. Subsequently, the pulser unit 46 generates a DC bias pulse signal based on the DC bias voltage control signal, amplifies the signal obtained by adding the low-voltage DC bias pulse signal and the low-voltage RF signal, generates the pulse of the waveform wherein the high-voltage RF signal is superimposed upon the high-voltage DC bias voltage, and outputs the pulse to the capacitive ultrasonic transducer units 38 side. The timing control in this case is performed by the control signal from a control circuit 52.

Thus, a DC bias voltage is generated only for a short period of time, whereby the effective value of the DC bias voltage can be reduced and used. Also, a DC bias voltage is generated only for a short period of time, whereby power consumption within the generating circuit thereof can be reduced.

Therefore, an advantage that facilitates reduction in the size and the like of the respective electronic parts making up the ultrasonic transducer and transducer control circuit block 32, or high-density mounting can be provided.

On the other hand, the reception signal amplified by the receiver 47 made up of a high input impedance charge amp is converted into low impedance, following which the signal is input to a filter making up a filter unit 55 within the ultrasonic diagnostic equipment 23 via an A/D converter 54 making up an A/D conversion unit 53, and the signal line of the cable 36.

Note that with the present embodiment, the A/D conversion unit 53 is provided at the ultrasonic transducer and transducer control circuit block 32 side, but may be provided at the ultrasonic diagnostic equipment 23 side.

With the present embodiment, the A/D conversion unit 53 is provided at the ultrasonic transducer and transducer control circuit block 32 side, whereby the reception signal can be converted into a digital signal, and consequently, deterioration at the time of transmission by the cable 36 is reduced. Even in the event that the insertion portion 26 is long, a signal having good S/N is transmitted to the ultrasonic diagnostic equipment 23 side almost without being affected by the length thereof.

The filter unit 55 extracts ultrasonic echo signal components. The properties of the filter are determined by the control circuit 52. The signal passing through the filter unit 55 is input to a beam synthetic circuit 57 via a reception delay unit 56, and is subjected to beam synthesis.

The signal is subjected to beam synthesis by the beam synthetic circuit 57, following which it is input to a digital scan converter (abbreviated as DSC) 58, and is converted into a picture signal, following which it is output to an ultrasonic monitor 24, where the display screen of the ultrasonic monitor 24 is arranged so as to display an ultrasonic image.

Also, the receiver unit 48 is configured so as to be applied with a low-voltage DC bias voltage control signal from the DC bias voltage generating control circuit 59. The RF signal is input to the receiver unit 48 from the capacitive ultrasonic transducer element 37 to which the DC bias voltage is applied. The DC bias voltage applied to the capacitive ultrasonic transducer element 37 is arranged so as to be generated only for a period of time when the RF signal is input to the receiver unit 48 by the control signal from the control circuit 52.

The amplitude of the RF signal to be input is small at the time of reception, so with the present embodiment, an arrangement is made wherein the value of the DC bias voltage is reduced at the time of reception as compared with the time of transmission to reduce the effective value thereof, thereby retaining the above advantage (reduction of power consumption).

Note that as illustrated in FIG. 3, the control circuit 52 controls each of the cyclic selection circuit 43, transmission delay unit 49, transmission waveform generating circuit 50, DC bias voltage generating control circuit 51, filter unit 55, reception delay unit 56, beam synthesis circuit 57, and DC bias voltage generating control circuit 59. Also, the control circuit 52 is connected with a scan setting unit 60 made up of a selection switch and so forth, and a user can select a desired scan mode from radial scanning and sector scanning, and selectively set scan conditions by operating the scan setting unit 60.

FIG. 4 illustrates, according to the cross section of the ultrasonic transducer and transducer control circuit block 32 in FIG. 2, the cross section of the array-type capacitive ultrasonic transducer 33 formed along the cylindrical face, and the configuration of the transducer control circuit formed therein.

As illustrated in FIG. 4, the array-type capacitive ultrasonic transducer 33 is formed on the outer face of a cylindrical flexible printed circuit substrate (abbreviated as FPC substrate) 61, and also the transducer control circuit 34 is formed on the inner face of the FPC substrate 61.

In this case, with the capacitive ultrasonic transducer 33, the capacitive ultrasonic transducer units 38 are formed on the FPC substrate 61 such that both sides are sandwiched by inter-unit grooves 62. Also, the cross-sectional portion in FIG. 4 in the capacitive ultrasonic transducer units 38 becomes the capacitive ultrasonic transducer elements 37 making up the units 38.

Also, the inner side of the FPC substrate 61 is provided with transducer control circuit units 63, which face the respective capacitive ultrasonic transducer units 38, for performing signal processing such as selection control, driving, amplifying, and the like corresponding to the capacitive ultrasonic transducer units 38.

The transducer control circuits 63 are also formed on the FPC substrate 61 such that both sides of each of the transducer control circuit units 63 are sandwiched with inter-unit grooves 64.

Note that as described with a later-described manufacturing method, a circuit block is formed from an integrated circuit wherein the capacitive ultrasonic transducer units 38 and the transducer control circuit units 63 are formed integrally on each face of the sheet-shaped FPC substrate 61 in a state in which the inter-unit grooves 62 and 64 are not formed so as to separate the capacitive ultrasonic transducer units 38 and the transducer control circuit units 63 by a dicing saw or the like, and this circuit block is processed in a cylindrical shape to form the cylindrical ultrasonic transducer and transducer control circuit block 32 illustrated in FIG. 4.

FIG. 5 illustrates the capacitive ultrasonic transducer unit 38 as viewed from the arrow A direction in FIG. 4. The capacitive ultrasonic transducer units 38 are each formed on the FPC substrate 61 by the m capacitive ultrasonic transducer elements 37 having a suitable thickness (height) of which cross-sectional configuration is illustrated in FIG. 6 being arrayed in the axial direction of the cylinder.

FIG. 6 illustrates the cross-sectional configuration of the capacitive ultrasonic transducer elements 37 based on the B-B-line cross section in FIG. 5.

Each of the capacitive ultrasonic transducer elements 37 is configured of, for example, the four capacitive ultrasonic transducer cells 44 of 2 lines by 2 rows. The upper faces of the respective four capacitive ultrasonic transducer cells 44 are each attached with an upper electrode 65, and these four upper electrodes 65 become an upper common ground electrode 66 which is commonly connected and grounded.

Each of the capacitive ultrasonic transducer cells 44 includes, for example, a hollow portion 72 made up of an insulation material 722 provided on a silicon substrate 71 using a process such as sacrifice etching or the like, and the portion covering the upper face of the hollow portion 72 is reduced to a thin film shape, thereby forming a membrane portion 73 which can vibrate. Also, the upper face of the membrane portion 73 is provided with the upper electrode 65, and the four upper electrodes 65 making up the capacitive ultrasonic transducer element 37 as a unit are connected to a ground electrode pad 75 provided on the bottom face (back face) of the silicon substrate 71 by a connector wiring 74 which is wired within an inter connect hole provided between the adjacent hollow portions 72. Note that the connector wiring 74 at a portion passing through the low-resistance silicon substrate 71 is insulated from the silicon substrate 71.

Also, the bottom face of each of the hollow portions 72 is disposed with a lower electrode 76, and the four lower electrodes 76 making up the capacitive ultrasonic transducer element 37 as a unit are mutually conductive via the low-resistance silicon substrate 71.

The lower electrodes 76 are divided for individual cells, and are subjected to ohmic contact on the low-resistance silicon substrate 71, so the four lower electrodes 76 are connected so as to have the same potential in increments of element via the low-resistance silicon substrate 71.

The four lower electrodes 76 are conductive with a signal input electrode pad 77 provided on the bottom face of the low-resistance silicon substrate 71 under the one hollow portion 72.

Also, the bottom face and side face portions of the low-resistance silicon substrate 71 which are externally exposed are covered with an insulating film 711.

According to such a configuration, a condenser configuration is formed between the upper electrode 65 and the lower electrode 76. The present embodiment includes an electric-acoustic conversion function wherein a high-voltage RF signal is superimposed on and applied to a DC bias voltage, whereby an ultrasonic wave can be generated by the RF signal, and also the membrane causes ultrasonic vibration by an ultrasonic signal, and the ultrasonic vibration is converted into a charge signal corresponding thereto by application of a DC bias voltage.

With the present embodiment, the capacitive ultrasonic transducer elements 37 are made up of the multiple capacitive ultrasonic transducer cells 44, whereby electric-acoustic conversion and acoustic-electric conversion can be performed effectively even with a high frequency, and a high-resolution ultrasonic image can be obtained.

FIG. 7 illustrates the configuration of the transducer control circuit unit 63 as viewed from the arrow C direction in FIG. 4. Also, FIG. 8 illustrates a configuration example of the transducer control circuit element based on the D-D-line cross section in FIG. 7.

As illustrated in FIG. 7, the transducer control circuit unit 63 formed on the FPC substrate 61 is made up of the m transducer control circuit elements 81 each formed at the positions corresponding to the capacitive ultrasonic transducer elements 37 described with FIG. 5.

The cylindrical inner face side of the ultrasonic transducer and transducer control circuit block 32 in each of the transducer control circuit elements 81 is provided with an electrode pad 82 (FIG. 7 illustrates one electrode pad for facilitating description, but as illustrated in FIG. 8, for example, there may be three electrode pads 82a, 82b, and 82c). Also, the outer face side of the FPC substrate 61 side in each of the transducer control circuit elements 81 is also provided with an electrode pad 83 and a ground electrode pad 84, as illustrated in FIG. 8.

As illustrated in FIG. 8, the transducer control circuit element 81 is made up of a transducer first control circuit 85 and a transducer second control circuit 86, for example.

The transducer first control circuit 85 makes up, for example as illustrated in FIG. 3, the transducer element selection switch 42, and a part of the cyclic selection circuit 43 for turning on/off the transducer element selection switch 42.

On the other hand, the transducer second control circuit 86 makes up, for example, the one pulser 45, one receiver 47, DC bias voltage generating circuit 51, 59, and one A/D converter 54 in FIG. 3.

In this case, the transducer first control circuit 85 side is formed so as to correspond to each of the capacitive ultrasonic transducer elements 37. On the other hand, the transducer second control circuit 86 side is configured so as to have each one of the pulsers 45 and so forth in one of the transducer control circuit units 63.

As illustrated in FIG. 8, the outer circumferential face of the transducer control circuit element 81 is covered with ground coating 87 wherein the outer circumferential face of an electroconductive film to be grounded is subjected to insulating coating, which prevents noise from being mixed in the inside thereof, and also prevents noise from being radiated from the inside to the outside.

Next, the manufacturing method of the ultrasonic transducer and transducer control circuit block 32 according to the present embodiment will be described with reference to FIG. 9A through FIG. 9G.

On both sides of the FPC substrate 61 on which a predetermined pattern is formed such as illustrated in FIG. 9A a transducer control circuit IC substrate 91 and an array-type capacitive ultrasonic transducer 92 prior to processing are mounted such as illustrated in FIG. 9B.

Subsequently, dicing grooves 93 are formed on the transducer control circuit IC substrate 91 which is the upper face side by a dicing saw or the like.

Thus, the dicing grooves 93 are formed on the transducer control circuit IC substrate 91 by a dicing saw or the like, whereby k transducer control circuit units 63 are formed such as illustrated in FIG. 9C.

Subsequently, the upper face and the lower face are reversed such as illustrated in FIG. 9D. With the state in FIG. 9D, upon dicing grooves 94 being formed on the array-type capacitive ultrasonic transducer 92 prior to processing which is the upper face side of the FPC substrate 61 by a dicing saw or the like, the k array-type capacitive ultrasonic transducer units 3 8 are formed such as illustrated in FIG. 9E.

Thus, the dicing grooves 93 and 94 are formed on the transducer control circuit IC substrate 91 and the array-type capacitive ultrasonic transducer 92 prior to processing mounted on the both sides of the FPC substrate 61 by a dicing saw respectively, which is further bent such as illustrated in FIG. 9F, and subsequently is bent to be changed into a cylindrical face shape which can be accommodated within the sheath tip member 31, and thus the cylindrical face shape illustrated in FIG. 9G is completed. Subsequently, as illustrated in FIG. 9G, a columnar third transducer control circuit 95 for example is disposed in the hollow portion of the inner side of the cylindrical face, and this third transducer control circuit 95 and the inner face of the transducer control circuit units 63 are connected with wirings 96.

Also, a circular void portion between the outer circumferential face of the columnar third transducer control circuit 95 and the inner circumferential face of the transducer control circuit units 63 is filled with a thermal conductive resin 97 having excellent thermal conductivity and also insulation to fix the columnar third transducer control circuit 95.

Note that as for the thermal conductive resin 97, a compound resin can be employed wherein fine powders of either of silicon carbide (SiC) or aluminum nitride (AlN) are dispersed into one of an epoxy resin, silicone resin, urethane resin, and acrylic resin, or a mixed resin.

The operation for generating an ultrasonic beam using the capacitive ultrasonic probe device 3 thus configured will be described with reference to FIG. 10A through FIG. 10E and FIG. 11.

Upon turning on the power, as illustrated in FIG. 3, the control circuit 52 transmits a timing signal having a predetermined cycle Trep such as illustrated in the top in FIG. 10A to the transmission waveform generating circuit 50, in sync with this signal the transmission waveform generating circuit 50 generates a transmission RF signal in a pulse shape such as illustrated in the bottom in FIG. 10A, and outputs this to the transmission delay unit 49.

The transmission delay unit 49 is formed with m delay circuits of which delay time is set depending on the delay time setting signal from the control circuit 52. The m delay circuits delay the transmission RF signals to be input by delay time each set thereto, and output the delayed transmission RF signals.

Therefore, the transmission delay unit 49 gives delay time and so forth to each of the elements within the same unit, and performs beam focusing and beam sector scanning for example.

For example, in the event of beam focusing employed for ordinary radial scanning or the like, the transmission delay unit 49 gives delay time that forms a circular arc 101 illustrated in the dashed-two dotted line in FIG. 10B as to the transmission RF signal at the bottom of FIG. 10A.

Subsequently, the respective delayed transmission RF signals are amplified by passing through the pulsers 45, and result in being applied to the k respective capacitive ultrasonic transducer elements 37 within the capacitive ultrasonic transducer unit 38 which has been turned on.

In this case, following the above low-voltage RF signal and a low-voltage DC bias voltage control signal being superimposed and controlled, the respective pulsers 45 of the pulser unit 46 amplifies this superimposed signal. The DC bias voltage control signal is formed within the pulser unit 46 in response to input of a control signal for setting the pulse polarity and pulse width and the like of a DC bias voltage, and is applied to the respective capacitive ultrasonic transducer elements 37 within the capacitive ultrasonic transducer unit 38 which has been turned on.

That is to say, the low-voltage transmission RF signal group in FIG. 10B becomes the high-voltage driving RF signal group illustrated in FIG. 10C by the pulser unit 46.

Note that in FIG. 10B and FIG. 10C, the vertical direction of page space becomes the array direction of the m capacitive ultrasonic transducer elements 37 within the unit 38.

As described above, a DC bias voltage is added, so that upon the driving signal waveform illustrated in FIG. 10C being enlarged and illustrated, this driving signal waveform becomes such as illustrated in FIG. 11. That is to say, with this driving signal waveform, high-voltage Vrf RF signal components are superimposed upon near the center of the pulse in the pulse-shaped DC bias waveform to which a high-voltage DC bias voltage Vdc is applied.

The wavefront of an ultrasonic wave to be transmitted to an organism from the m capacitive ultrasonic transducer elements 37 becomes a circular arc shape such as illustrated in FIG. 10D, and the focusing point of an ultrasonic beam is the middle position in the array direction and also the direction orthogonal to the array direction (horizontal direction in FIG. 10D). Note that the element array direction is the direction in parallel with the insertion axis in the cylindrical face.

In the event of radial scanning, the transducer element selection units 41 to be turned on are sequentially moved by the cyclic selection circuit 43. Therefore, the units 38 disposed in the circumferential direction of the cylindrical face sequentially transmit an ultrasonic wave, whereby radial scanning is performed wherein an ultrasonic wave is sequentially transmitted or received radially around the insertion axis.

On the other hand, an arrangement may be made wherein the delay time setting signal to be provided to the transmission delay unit 49 from the control circuit 52 is modified, whereby sector scanning can be performed in the insertion axis direction.

That is to say, sector scanning can be performed by assuming that the center of a circular arc indicating the distribution of delay time illustrated in FIG. 10B is regarded as the center of the element array direction, and scanning is performed in that array direction.

FIG. 10E illustrates when an ultrasonic wave is transmitted toward one of the element array direction in the event of sector scanning. Thus, in the event of performing sector scanning, the delay time setting signal to be provided to the transmission delay unit 49 from the control circuit 52 is changed for each predetermined time Trep, and also selection of a unit is circulated while performing such scanning within the ultrasonic transducer unit, whereby radial scanning can be performed while performing sector scanning.

On the other hand, as for a unit to be driven, the same unit is repeatedly selected. Thus, sector scanning can be performed in the insertion axis direction.

Thus, the m capacitive ultrasonic transducer elements 37 are simultaneously driven with a phase difference, whereby focusing of an ultrasonic beam, and sector scanning can be performed, and transmission can be performed as to the inspection target portion side such as an affected portion or the like within a body cavity. Also, beam synthesis or the like wherein the reflected ultrasonic wave thereof is provided with a phase difference is performed, whereby an ultrasonic echo signal which focuses a particular point can be obtained.

Therefore, according to the present embodiment, radial scanning around the central axis and sector scanning in the insertion axis direction can be performed simultaneously, and consequently, three-dimensional ultrasonic images within a body cavity can be obtained.

Also, in the event that duration in which a DC bias voltage is applied is a short period of time in the vicinity of the time when applying an RF driving signal, or duration in which an echo signal is input at the time of reception, reducing the value thereof reduces the effective value thereof, thereby enabling use within a body cavity.

Also, the electronic circuit elements of the ultrasonic transducer and transducer control circuit block 32 are reduced in size or mounted in the high density in the vicinity of the respective capacitive ultrasonic transducer elements 37, whereby losses and noise at the time of signal transmission by the coaxial cable can be reduced. Accordingly, the outside diameter of the ultrasonic probe head portion 27 and the like in the event of insertion into a body cavity can be reduced, and an endoscope of which insertion portion is slender and small in the channel diameter thereof can be employed, and thus pain inflicted on a patient at the time of insertion can be reduced as well.

Also, with radial scanning, selection of a transducer unit is performed by the control signal from the cyclic selection circuit 43, so it is sufficient to prepare for m coaxial cables relating to sector scanning, and consequently, it is sufficient to prepare for an extremely small number of coaxial cables in proportion to the number of transducer elements to be controlled.

Note that with the present embodiment, an arrangement has been made wherein the columnar third transducer control circuit 95 is disposed at the hollow portion at the inner side of the cylindrical face as shown in FIG. 9G, and this third transducer control circuit 95 and the transducer control circuit units 63 are connected by the wirings 96, but an arrangement may be made such as the following modifications.

For example, a hollow cylindrical shape including the third transducer control circuit 95 is employed. In this case, the inside diameter of the hollow portion at the inner side of the cylindrical shape may be small. An arrangement may be made wherein one face of a second FPC substrate is connected with the tip side of a flat cable making up the cable 36, following which this second FPC substrate is bent so as to become a cylindrical shape, electrode pads formed on the outer circumferential side of the cylindrical face thereof are connected to the inner face of the transducer control circuit units 63 by flip chip bonding or the like, and the inner circumferential face of this FPC substrate is filled with the insulating thermal conductive resin 97.

Alternatively, an arrangement may be made wherein following the state illustrated in FIG. 9E, this second FPC substrate is connected to the FPC substrate 61, and then is bent so as to become a cylindrical shape. In this case, electrical connections can be performed in a flat-plate state, thereby providing an advantage for facilitating connection work.

The present embodiment described above has the following advantages.

The circuits such as pulsers, receivers, and so forth are disposed in the vicinity of the respective ultrasonic transducer elements, thus great signal losses due to the cable and noise to be superimposed on the cable can be reduced.

Also, radial scanning around the insertion axis and sector scanning in the insertion axis direction can be performed simultaneously, whereby three-dimensional ultrasonic images within a body cavity can be obtained.

Also, three-dimensional ultrasonic images can be obtained with a small number of wirings. For example, when assuming that the above number of elements m=64, and the above number of units k=256, a conventional example requires 16,384 cables, but with the present embodiment, it is sufficient to prepare for (256+α) coaxial cables. Here, α denotes the number of cables for control signals.

Second Embodiment

Figure 12:
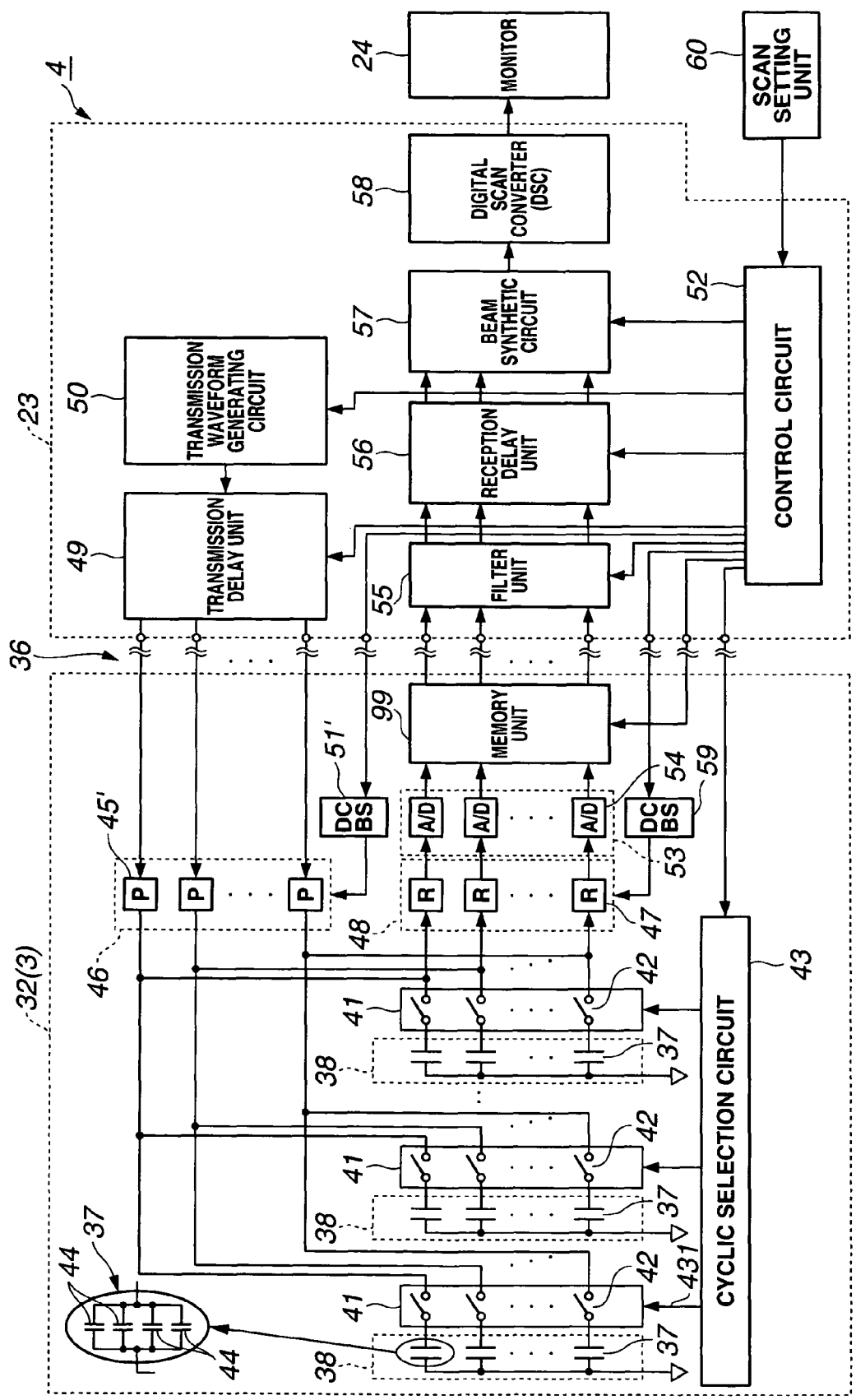
FIG. 12 is a block diagram illustrating the electric system configuration of an ultrasonic diagnosis device including a capacitive ultrasonic probe device according to a second embodiment of the present invention.
Figure 13:
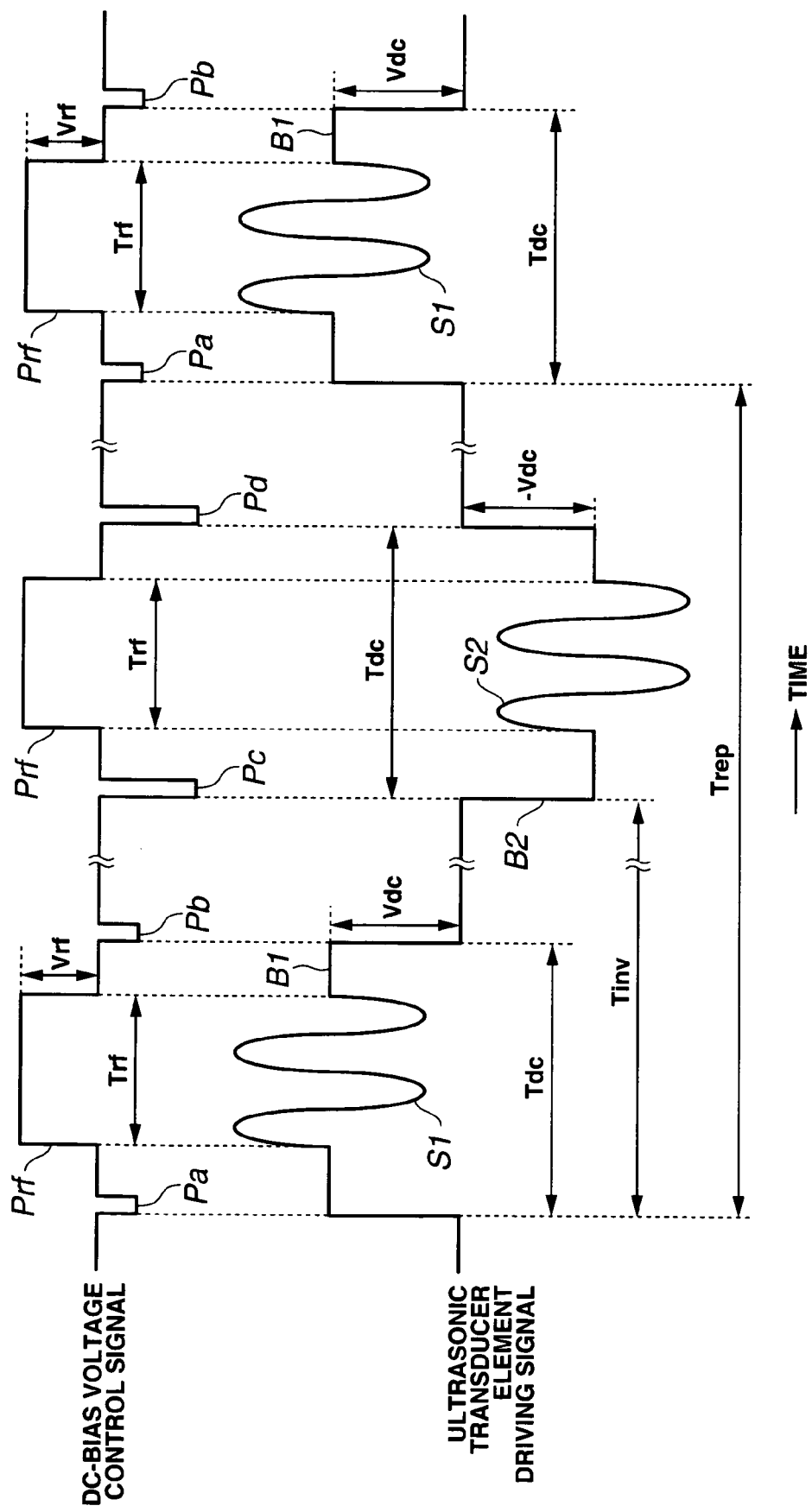
FIG. 13 is a diagram illustrating a DC-bias waveform control signal and an ultrasonic transducer element driving signal in an operation example at tissue harmonic imaging by pulse inversion.
Figure 14A:
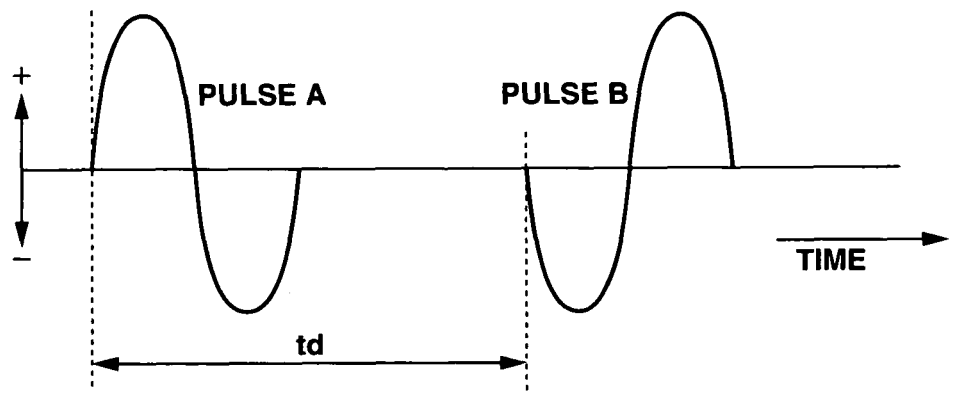
FIG. 14A is a principled explanatory diagram of pulse inversion.
Figure 14B:
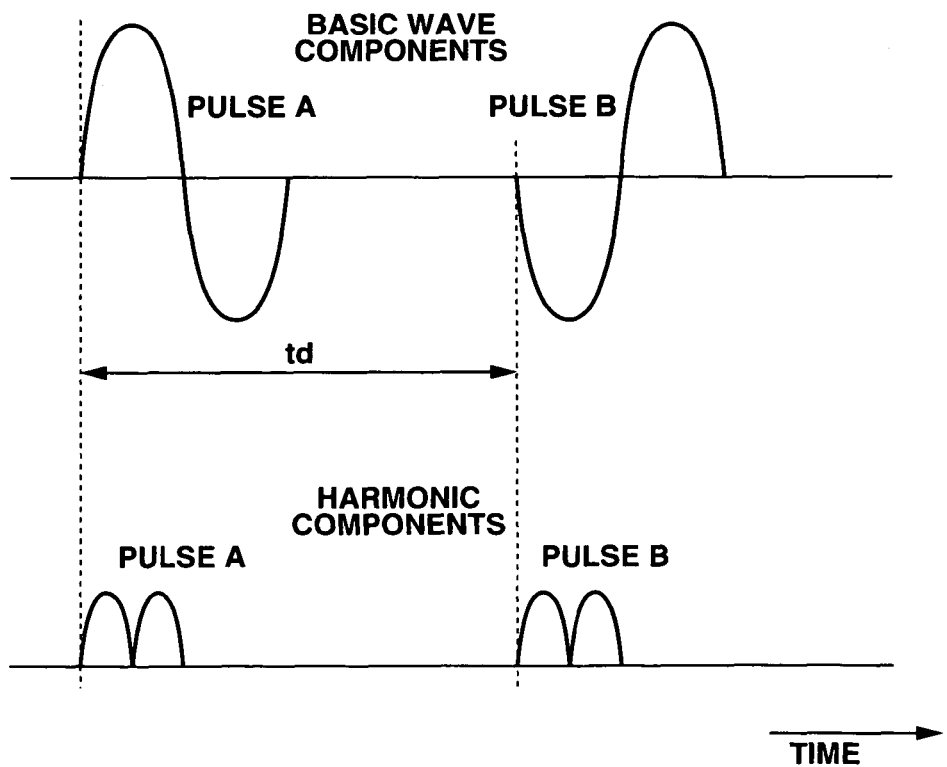
FIG. 14B is a principled explanatory diagram of pulse inversion.

Next, a second embodiment of the present invention will be described with reference to FIG. 12 through FIG. 14B. FIG. 12 illustrates the electrical system configuration of an ultrasonic diagnostic device including the second embodiment, FIG. 13 illustrates a DC bias voltage control signal and an ultrasonic transducer element driving signal in an operation example in tissue harmonic imaging (abbreviated as THI) using pulse inversion, and FIG. 14A and FIG. 14B illustrate diagrams for describing the principle of pulse inversion, i.e., the ultrasonic transducer element driving signal and extraction of harmonic components from a reception signal.

The ultrasonic diagnostic device 4 illustrated in FIG. 12 has a configuration wherein a memory unit 99 is further provided at the output portion of the A/D conversion unit 53 in the ultrasonic transducer and transducer control circuit block 32 in FIG. 2, and writing and reading out of an echo signal at the memory unit 99 is controlled by the control circuit 52.

That is to say, the capacitive ultrasonic probe device 3 according to the present embodiment has a configuration wherein the memory unit 99 is further provided in the capacitive ultrasonic probe device 3 according to the first embodiment. Note that the memory unit 99 may be provided at the ultrasonic diagnostic equipment 23 side.

Also, with the present embodiment, a DC bias voltage generating control circuit 51' for generating positive and negative polarity DC bias voltage control signals is employed instead of the DC bias voltage generating control circuit 51 in FIG. 3. Note that the DC bias voltage generating control circuit 51' is abbreviated as DCBS 51' for the sake of simplification in FIG. 12. Also, respective pulsers 45' in the pulser unit 46 according to the present embodiment include a delay circuit for delaying a driving signal by predetermined duration Tinv, whereby a driving signal can be subsequently output with delay of only this duration Tinv following the preceding driving signal.

With the present embodiment, the control circuit 52 outputs the DC bias voltage control signal illustrated in the top of FIG. 13 to the pulser unit 46 and the DC bias voltage generating control circuit 51', and the pulser unit 46 generates an ultrasonic transducer element driving signal for THI such as illustrated in the bottom of FIG. 13 based on the received DC bias voltage control signal. The others are the same as the first embodiment.

With the present embodiment, an arrangement is made wherein the same operation as the first embodiment can be performed, and also THI can be performed using pulse inversion by the memory unit 99 and so forth being provided.

In this case, a driving method such as illustrated in FIG. 13 can be employed. The top of FIG. 13 illustrates the low-voltage DC bias voltage control signal which the control circuit 51' outputs, and the bottom of FIG. 13 illustrates the high-voltage ultrasonic transducer element driving signal to be output from the pulser unit 46.

The operation principle in the event of performing harmonic imaging using pulse inversion will be described first with reference to FIG. 14A and FIG. 14B. FIG. 14A and FIG. 14B illustrate the principle diagrams of pulse inversion.

As illustrated in FIG. 14A, as for a driving signal, a double pulse made up of a pulse A, time difference td (corresponds to the duration Tinv in FIG. 13), and a pulse B having an opposite phase is applied to an ultrasonic transducer to transmit an ultrasonic wave to an organism tissue side. The transmission signal has the same waveform as that in FIG. 14A.

According to nonlinearity of organism tissue, as well as the fundamental wave components of an ultrasonic wave, a reception signal in which harmonic wave components having small acoustic pressure of several tens dB for example are mixed in the acoustic pressure of the fundamental wave components is obtained, and accordingly, there is the need to remove the fundamental wave components from the reception signal in which both are mixed. Thus, harmonic wave components alone can be extracted.

In this case, as shown in FIG. 14B, the pulses A and B of the fundamental wave components in the reception signal retain the same phase relation as that at the time of transmission, but the even-ordered harmonic wave components become the square root, fourth root, and so on of the fundamental wave, so that all become positive pulses A and B. The harmonic wave in FIG. 14B is illustrated with the second harmonic wave.

Therefore, the pulse A and pulse B of the fundamental wave components in the reception signal become zero when obtaining the sum of both by assuming that the time difference td is zero.

On the other hand, the harmonic wave components are doubled when obtaining the sum of both by assuming that the time difference td is zero.

Thus, the harmonic wave components alone can be extracted. Note that as for means for setting the time difference td to zero, the memory unit 99 in FIG. 12 according to the present embodiment can be employed.

That is to say, the preceding reception pulse A is temporarily stored in the memory unit 99, the reception pulse A is read out from the memory unit 99 at the point of the subsequent reception pulse B arriving, and the sum between the reception pulse A and the reception pulse B is obtained, whereby the fundamental wave components can be set to zero, and the even-ordered harmonic wave components can be doubled and obtained.

FIG. 14A and FIG. 14B are principle diagrams, which is a method not depending on a capacitive type. On the other hand, the method illustrated in FIG. 13 is a capacitive type, and accordingly, a driving signal having the same phase is superimposed on a DC bias voltage pulse having a different polarity, and is applied to the capacitive ultrasonic transducer elements 37, whereby an ultrasonic wave having an opposite phase is generated, and transmitted to an organism side.

A reception signal is arranged to be obtained in a state of the DC bias voltage of one polarity being applied thereto at the time of reception, whereby the same operation in the case described with FIG. 14A and FIG. 14B can be obtained.

Next, a method for generating a driving signal for pulse inversion will be described with reference to FIG. 13.

With the present embodiment, upon the low-voltage DC bias voltage control signal from the DC bias voltage generating control circuit 51' being input to the pulsers 45' in sync with a +DC bias activating timing pulse Pa in the DC bias voltage control signal illustrated in the top of FIG. 13, the pulsers 45' add this with a low-voltage RF signal to be input immediately following thereof to amplify this, thereby generating a high-voltage driving signal such as illustrated in the bottom of FIG. 13.

That is to say, the pulsers 45' output a high-voltage DC bias voltage pulse B1 of which voltage value becomes positive of +Vdc such as illustrated in the bottom of FIG. 13 in sync with the +DC bias activating timing pulse Pa, and at this time, outputs a driving signal having a wave in which a high-voltage RF signal S1 is superimposed on the DC bias voltage pulse B1.

The generating duration Tdc of the high-voltage DC bias voltage pulse B1 is from the DC bias activating timing pulse Pa to a +DC bias stopping timing pulse Pb that stops output thereof.

Also, with the high-voltage RF signal S1, the signal voltage value immediately following the +DC bias activating timing pulse Pa amplifies a low-voltage RF signal to be input at an RF generating timing pulse Prf, so that the generating duration Trf of the RF generating timing pulse Prf thereof is shorter than the generating duration Tdc of the DC bias voltage pulse B1.

Thus, the driving signal in which the RF signal S1 is superimposed on the positive DC bias voltage pulse B1 is applied to the capacitive ultrasonic transducer elements 37. Subsequently, the capacitive ultrasonic transducer elements 37 convert this driving signal into an ultrasonic wave, and transmit the ultrasonic wave thereof to an organism tissue side within a body cavity.

Following the predetermined duration Tinv which is a half of the predetermined duration Trep corresponding to a transmission range capable of generating an image using the ultrasonic wave thereof, the DC bias voltage control signal becomes a signal accompanying a −DC bias activating timing pulse Pc such as illustrated in the top of FIG. 13. The voltage of this −DC bias activating timing pulse Pc differs from the value of the above +DC bias activating timing pulse Pa.

Subsequently, upon a low-voltage DC bias control signal being input to the pulsers 45' from the DC bias voltage generating control circuit 51' in sync with the −DC bias activating timing pulse Pc, the pulsers 45' add this with a low-voltage RF signal to be input immediately following thereof to amplify this, thereby outputting a high-voltage driving signal such as illustrated in the bottom of FIG. 13.

In this case, the pulsers 45' output a DC bias voltage pulse B2 of which voltage value becomes negative of −Vdc such as illustrated in the bottom of FIG. 13 in sync with the −DC bias activating timing pulse Pc, and stop output in sync with −DC bias stopping timing pulse Pd. The generating duration of the DC bias voltage pulse B2 is equivalent to the Tdc.

Also, the pulsers 45' amplify a low-voltage RF signal to output a high-voltage RF signal S2 in sync with the RF signal generating timing pulse Prf of which signal voltage value is the Vrf immediately following the −DC bias activating timing pulse Pc during the generating duration Tdc of the above DC bias voltage pulse B2, such as illustrated in the bottom of FIG. 13. In this case, the pulsers 45' amplify the low-voltage RF signal using an unshown delay circuit to generate a high-voltage RF signal S2 having the same waveform as the high-voltage RF signal S1.

The generating duration Trf of the RF generating timing pulse Prf is shorter than the generating duration Tdc of the DC bias voltage pulse B2.

Subsequently, a driving signal in which the RF signal S2 is superimposed on the negative DC bias voltage pulse B2 is applied to the capacitive ultrasonic transducer elements 37. Subsequently, the capacitive ultrasonic transducer elements 37 convert the driving signal into an ultrasonic wave, and transmit the ultrasonic wave thereof to an organism tissue side of a body cavity.

In this case, in opposition to the case of the preceding positive DC bias voltage pulse B1, the RF signal S2 is applied to the capacitive ultrasonic transducer elements 37 in a state of the negative DC bias voltage pulse B2 being applied thereto, so in this case, the ultrasonic wave having the reverse phase (shifted 180 degrees) of the preceding ultrasonic wave is generated.

Thus, the capacitive ultrasonic transducer elements 37 are driven by the double pulse. Subsequently, in the event of receiving the preceding transmitted ultrasonic wave, the capacitive ultrasonic transducer elements 37 temporarily store the received ultrasonic wave in the memory unit 99. Subsequently, the RF signal received at the timing of elapsing the predetermined duration Tinv, and the received RF signal read out from the memory unit 99 are added, and thus the difference in phase can be cancelled out mutually since both have a reverse phase in the received RF signal of the fundamental wave, whereby doubled harmonic wave (particularly, the second harmonic wave, or even-ordered harmonic wave) components can be obtained.

The same processing as in the case of the fundamental wave is performed using the harmonic wave components thereof, whereby THI ultrasonic tomograms can be obtained.

Thus, according to the present embodiment, the same operation advantages as the first embodiment can be obtained, and also the present embodiment can be applied to the case of obtaining THI ultrasonic tomograms as well.

Note that with the above description, the cyclic selection circuit 43 is configured so as to turn on/off all of the arbitrary transducer element selection switches 42 belonged to each of the transducer element selection units 41, but is not restricted to this, so the cyclic selection circuit 43 may be configured so as to turn on/off an arbitrary transducer element selection switch 42 within the transducer element selection units 41.

In this case, linear scanning can be performed as well as radial scanning and sector scanning.

Note that an embodiment and the like configured by partially modifying the above respective embodiments are also belonged to the present invention. For example, with the first embodiment, the capacitive ultrasonic transducer elements 37 are two-dimensionally formed on the entire circumference of the cylindrical face, but an arrangement wherein the capacitive ultrasonic transducer elements 37 are formed on a part of the cylindrical face is also belonged to the present invention.

A method for manufacturing a capacitive ultrasonic probe device may comprise the following steps S1 through S7:

A step for joining a silicon substrate on which many capacitive ultrasonic transducer cells are arrayed and formed to one side of a flexible printed substrate, and joining a silicon substrate on which many driving control circuits are arrayed and formed to the other face side thereof (S1);

subsequently, a step for subjecting the silicon substrate on which many driving control circuits are arrayed and formed to dicing with a depth where the cutting edge of a dicing reaches the flexible printed substrate surface in increments of unit (S2);

further, a step for subjecting the silicon substrate on which many capacitive ultrasonic transducer cells are arrayed and formed to dicing with a depth where the cutting edge of a dicing reaches the flexible printed substrate surface in increments of units (S3);

subsequently, a step for subjecting a FPC exposure portion to masking, and subjecting the silicon substrates to metal film coating to subject the side faces of both units to electroconductive coating processing (S4);

a step for disposing this within a tube having a predetermined inside diameter, and forming a tube shaped structure made up the cylindrical shaped flexible printed substrate, driving control circuit unit, and capacitive ultrasonic transducer unit along the tube wall (S5);

further, a step for disposing another driving control integrated circuit substrate at the center portion of the inside diameter portion, performing wiring with the other driving control circuit units, and connection of a coaxial cable, and then filling a compound resin which excels in insulation and thermal conductivity therein (S6); and subsequently, a step for packaging the tubular shaped structure in a sheath, and filling an acoustic binding agent in the space between the tubular shaped structure and the sheath, and finally sealing this (S7).

Third Embodiment

Figure 15:
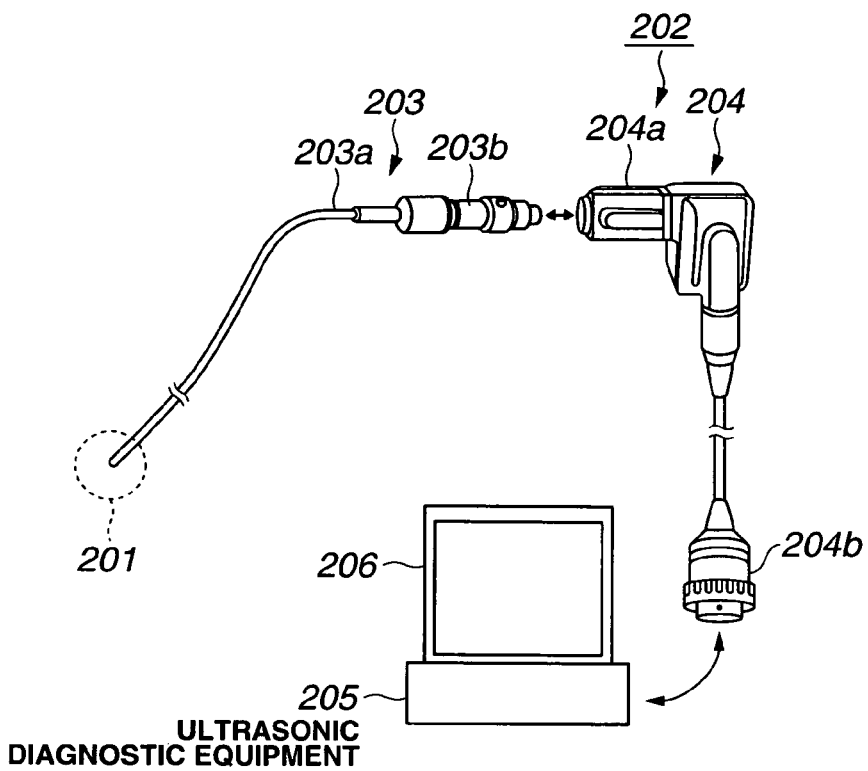
FIG. 15 is a diagram illustrating a capacitive ultrasonic probe device according to a third embodiment of the present invention.
Figure 16:
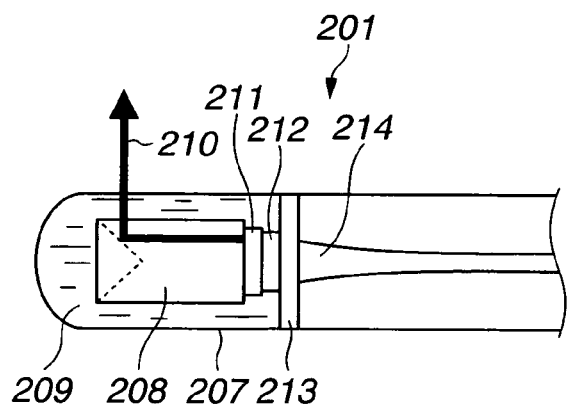
FIG. 16 is a diagram enlarging and illustrating the ultrasonic probe tip portion in FIG. 15.

FIG. 15 is a diagram illustrating a capacitive ultrasonic probe device according to a third embodiment of the present invention, and FIG. 16 illustrates an enlarged view of the ultrasonic probe tip portion in FIG. 15.

In FIG. 15, reference numeral 201 denotes an ultrasonic probe tip portion, 202 denotes a capacitive ultrasonic probe device, 203 denotes an ultrasonic probe main body, 203a denotes an insertion portion, 203b denotes a joint, 204 denotes a driving control unit, 204a and 204b denote joints, 205 denotes an diagnostic equipment, and 206 denotes a monitor.

The ultrasonic probe tip portion 201 includes an ultrasonic transducer serving as an ultrasonic sensor, the insertion portion 203a made up of a slender tube is inserted into an ultrasonic forceps hole, an ultrasonic image is observed while viewing an optical image at the tip protruding portion using an endoscope, which is a usage example. As for the ultrasonic transducer of the ultrasonic probe tip portion 201, a capacitive ultrasonic transducer is employed instead of a conventional piezoelectric ultrasonic transducer.

The configuration of the ultrasonic probe tip portion 201 is such as illustrated in FIG. 16. In FIG. 16, reference numeral. 201 denotes an ultrasonic probe tip portion, 207 denotes a sheath, 208 denotes an ultrasonic beam propagation direction conversion rod serving as an ultrasonic propagation medium, 209 denotes an acoustic binding solution, 210 denotes an ultrasonic beam, 211 denotes an ultrasonic transducer, 212 denotes a control circuit, 213 denotes a partition, and 214 denotes a coaxial cable bundle.

The control circuit 212 drives the ultrasonic transducer 211, the ultrasonic beam generated at the ultrasonic transducer 211 propagates the ultrasonic beam propagation direction conversion rod 208 made up of a member of which acoustic propagation losses are small such as glass or the like in the insertion axis direction, and is reflected at the tip portion of the rod 208 to be emitted to the outside of the sheath 207 via the acoustic binding solution 209. The sheath 207 is a tube of which tip is closed in a globular shape, and with the partition 213 as the boundary thereof, the acoustic binding solution 209 made up of water is filled in the left side in the drawing, which propagates an ultrasonic wave to the outside of the sheath without losses.

Figure 17:
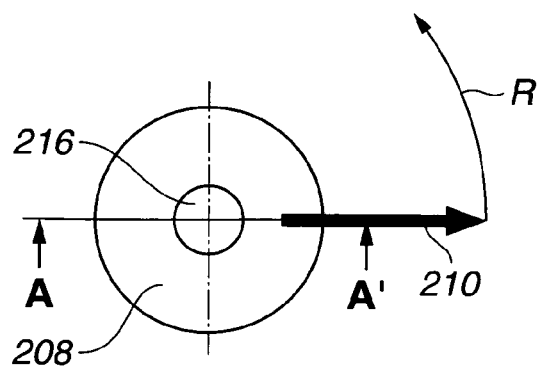
FIG. 17 is a top face view of the ultrasonic beam propagation direction conversion rod in FIG. 16.
Figure 18:
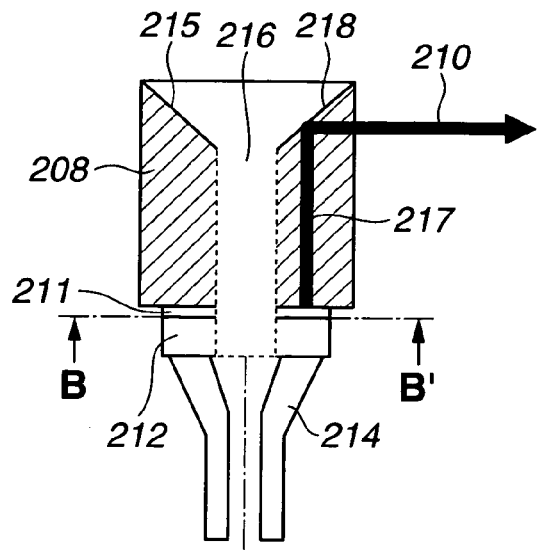
FIG. 18 is a cross-sectional view taken along the line A-A' in FIG. 17.

FIG. 17 is the top view in the respective portions of the ultrasonic beam propagation direction conversion rod 208, ultrasonic transducer 211, control circuit 212, and coaxial cable bundle 214. FIG. 18 is the A-A'-line vertical cross-sectional view in FIG. 17, and FIG. 19 is a diagram as viewed from the line B-B' in FIG. 18 (the plan view of the ultrasonic transducer portion).

With those diagrams, reference numeral 215 denotes an ultrasonic reflection face, 216 denotes a hollow hole, 217 denotes an intra-rod ultrasonic beam, 218 denotes an ultrasonic beam reflected point, and 219 denotes a rod bottom face.

The rod 208 is formed in a cylindrical shape of which the wall thickness is great, and the tip face thereof is hollowed out in a conical shape. As viewed from the cross section of FIG. 8, the tip face of the rod 208 is a shape including taper. The tip face of the rod 208 has an angular component (tilt) of 45 degrees for example in the insertion axis direction, and reflects an ultrasonic wave emitted and propagated in the insertion axis direction toward the direction of 90 degrees serving as a predetermined angle as to the insertion axis. Note that an angular component of 45 degrees is not restricted to this value, and can be changed into a different angle depending on a diagnostic portion as appropriate. The portion equivalent to the insertion axis of the rod 208 is the hollow hole 216. The bottom face 219 is formed flat, and the flat portion thereof is bonded with a ring-shaped ultrasonic transducer 211. The rod 208 and the ultrasonic transducer 211 are disposed and bonded so as to match the centers of the inside diameter circles of both. Further, the control circuit 212 is disposed in a ring shape so as to be adjacent to the ultrasonic transducer 211.

Figure 19:
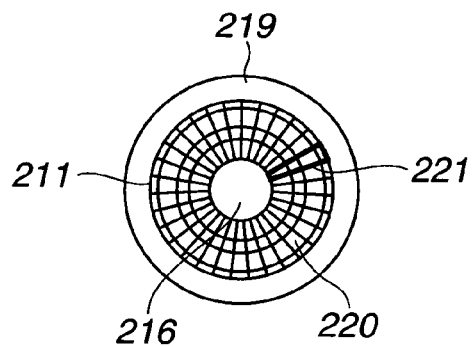
FIG. 19 is a view as viewed from the line B-B' in FIG. 18.

With regard to the ultrasonic transducer 211, as illustrated in FIG. 19, many capacitive ultrasonic transducer elements 221 made up of multiple (four in the drawing) capacitive ultrasonic transducer cells 220 are formed in the circumferential direction of the ring-shaped ultrasonic transducer.

Figure 20:
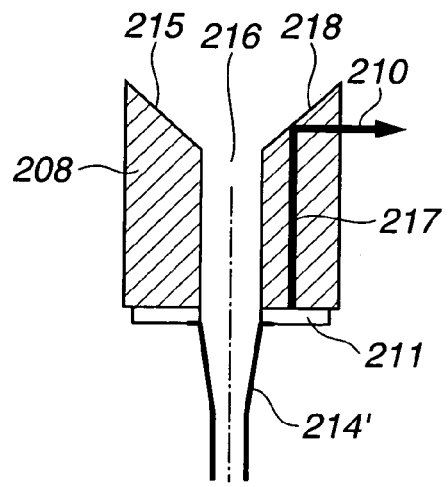
FIG. 20 is a cross-sectional view illustrating a state in which the control circuit and the bunch of a coaxial cable bundle to be connected thereto are removed in FIG. 18.

FIG. 20 illustrates a state in which the control circuit 212 and the line bundle of the coaxial cable bundle 214 to be connected to the control circuit 212 are removed from FIG. 18. Of the coaxial cable bundle 214, a line bundle 214' alone to be connected to the electrode of the ultrasonic transducer 211 is illustrated.

In such a state, upon the ultrasonic transducer 211 vibrating, the vibration thereof enters the ultrasonic beam propagation direction conversion rod 208, and propagates in the insertion axis direction. Subsequently, upon the vibration thereof being reflected at the conical reflected face 215 which is the tip face of the rod 208, the vibration is reflected toward the direction of 90 degrees as to the direction of the insertion axis. Upon successively scanning many capacitive ultrasonic transducer elements 221 in the rotational direction R (see FIG. 17) in increments of element, radial scanning can be performed while rotating the ultrasonic beam 210.

Note that as for the configuration of the ultrasonic probe tip portion illustrated in FIG. 17 through FIG. 20, the case of employing a piezoelectric ultrasonic transducer can be applied as well as the case of employing a capacitive ultrasonic transducer.

The conical processed face making up the ultrasonic reflected face is a convex curved face as viewed from the ultrasonic incident side, so the ultrasonic beam reflected there is converted into a fan beam. Accordingly, an acoustic focal point can be shifted remotely as compared with the probe having a conventional configuration employing a sheath having the same dimension and material, and an acoustic binding agent, thereby improving invasion depth. That is to say, the ultrasonic reflected face 215 has a curved face, which expands an ultrasonic beam, whereby an ultrasonic beam can be focused remotely even if there is an acoustic binding agent having a great lens effect. Expanding an ultrasonic beam results in improvement of invasion depth, which is convenient.

Figure 21:
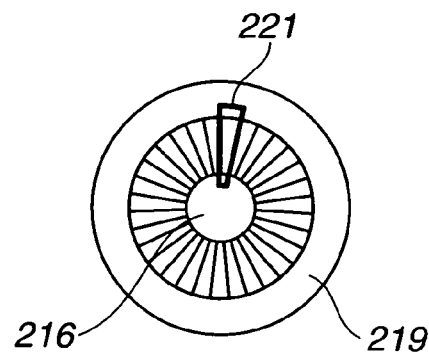
FIG. 21 is a plan view of an ultrasonic transducer disposed at the bottom face of the ultrasonic beam propagation direction conversion rod.
Figure 22:
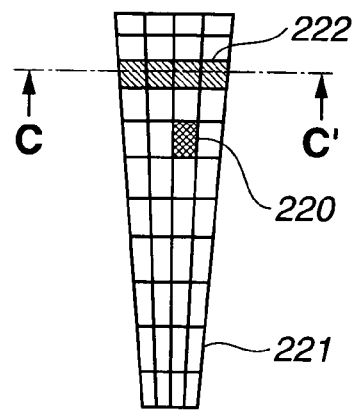
FIG. 22 is a diagram illustrating a detailed configuration example of the ultrasonic transducer element in FIG. 21.
Figure 23:
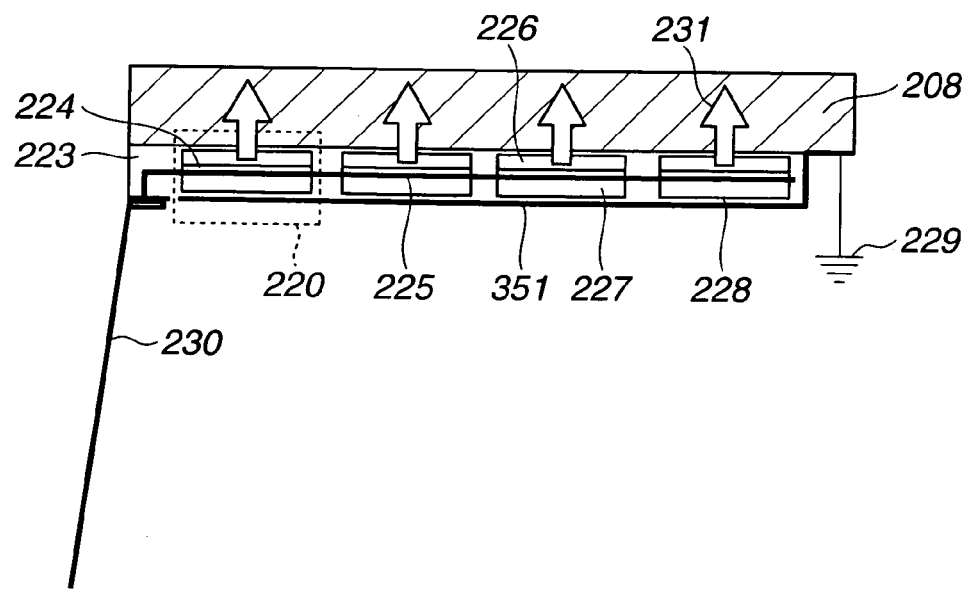
FIG. 23 is a longitudinal cross-sectional view which is equivalent to the C-C'-line cross-section in FIG. 22.

FIG. 21 illustrates a plan view of an ultrasonic transducer disposed on the bottom of the ultrasonic beam propagation direction conversion rod 208, FIG. 22 illustrates a detailed configuration example of the ultrasonic transducer element in FIG. 21, and FIG. 23 illustrates a cross-sectional view equivalent to the C-C'-line cross section in FIG. 22.

In FIG. 22, upon viewing the capacitive ultrasonic transducer element 221 in detail, the capacitive ultrasonic transducer element 221 is a group of the capacitive ultrasonic transducer cells 220. The capacitive ultrasonic transducer element 221 includes capacitive ultrasonic transducer sub elements 222 wherein multiple (four in the drawing) capacitive ultrasonic transducer cells 220 are arrayed in the lateral direction. Accordingly, the several capacitive ultrasonic transducer sub elements 222 collectively make up one unit such as the capacitive ultrasonic transducer element 221.

FIG. 23 is the cross section of the capacitive ultrasonic transducer sub element 222 thereof as viewed from the cutaway of the line C-C', wherein the four capacitive ultrasonic transducer cells 220 are arrayed.

In FIG. 23, reference numeral 220 denotes a capacitive ultrasonic transducer cell, 223 denotes a silicon substrate, 224 denotes a first membrane within a cavity, 225 denotes an electrode (for signals), 226 and 227 denote cavities, 228 denotes a second membrane, 229 denotes ground, 230 denotes a cable, 231 denotes an ultrasonic wave, and 351 denotes an electrode (for ground). Note that the air is filled in the cavities 226 and 227.

A quadrangular dashed line frame is the capacitive ultrasonic transducer cell 220, and the four cells 220 are arrayed. These four cells 220 each (not common in the four cavities) include the film of the internal membrane 224 so as to divide the corresponding cavity 227 into two. The electrode 225 is formed on one side of the internal membrane 224, which distinguishes the cavities 227 and 226. That is to say, the cavity is divided into the two sub cavities 227 and 226 with the intra-cavity membrane 224 as boundary. The other membrane 228 is not a film formed within the cavity, and is an external membrane. The internal membrane 224 and the external membrane 228 are both films created by silicon semiconductor process.

A portion making up capacitance (condenser) applies voltage to between the electrode 351 disposed on the external membrane 228 and the electrode 225 disposed on the internal membrane (intra-cavity membrane) 224 to generate electrostatic attraction force between both electrodes thereof. The ultrasonic wave 231 is generated only from the electrodes 225 and 351. The ultrasonic wave 231 is generated, but basically a propagation medium is the air. The acoustic impedance of the air is extremely small. On the other hand, the acoustic impedance of the rod 208 is extremely large. That is to say, it is necessary to perform acoustic matching as to the rod 208 having extremely high acoustic impedance. There is the need to form acoustic matching means such as changing acoustic impedance between the cavity 226 and the rod 208 gradually.

Figure 24:
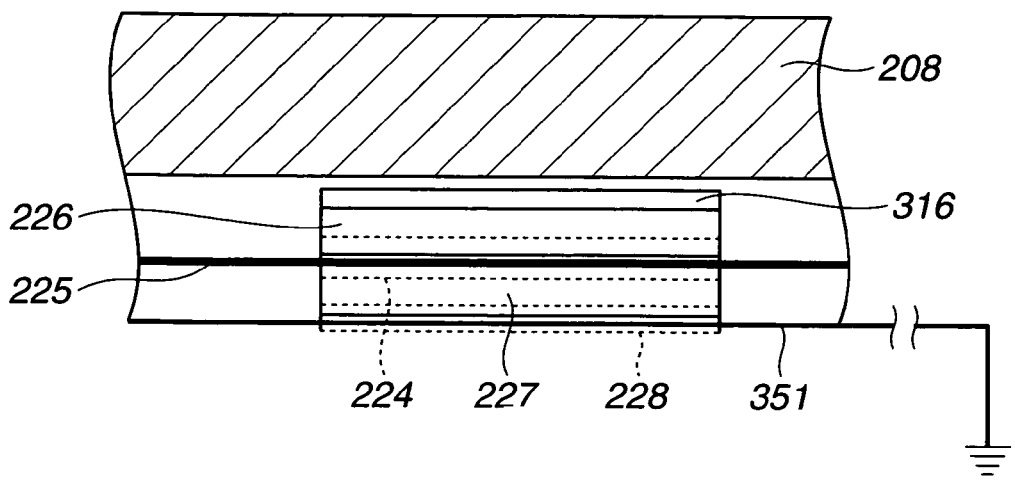
FIG. 24 is a diagram illustrating one example of acoustic matching means provided between the cavity and the rod.

FIG. 24 is a diagram illustrating one example of acoustic matching means provided between the cavity 226 and the rod 208. A configuration wherein an acoustic matching layer 316 is provided at a position near the bottom face of the rod 208 between the cavity 226 and the rod 208 is employed. In other words, the acoustic matching layer 316 is formed at the side near the cavity 226 and the rod 208. It is needless to say that as for such an acoustic matching layer, one or more acoustic matching layers such as changing acoustic impedance gradually may be provided.

Next, a method for manufacturing a capacitive ultrasonic transducer in the ultrasonic probe tip portion will be described with reference to FIG. 25A through FIG. 25J, including the formation of the acoustic matching layer 316.

With the manufacturing method illustrated in FIG. 25A through FIG. 25J, reference numeral 208 denotes an ultrasonic beam propagation direction conversion rod, 223 denotes a silicon substrate, 224 denotes a membrane film, 225 denotes a lower electrode (signal electrode), 226 denotes a cavity, 227 denotes a cavity, 316 denotes an acoustic matching layer, 317 denotes a separate member supporting portion, 322 denotes an etching portion, 324 denotes an interconnect via hole, 325 denotes an insulating film, 326 denotes a contact pad (for a common ground electrode (351)), 327 denotes a contact pad (for a signal electrode (225)), 328 denotes a membrane supporting portion, 329 denotes a sacrifice layer, 331 denotes a sacrifice layer removal hole, 333 denotes a membrane with a hole shielding film, and 351 denotes an upper electrode (common ground electrode).

Figure 25A:
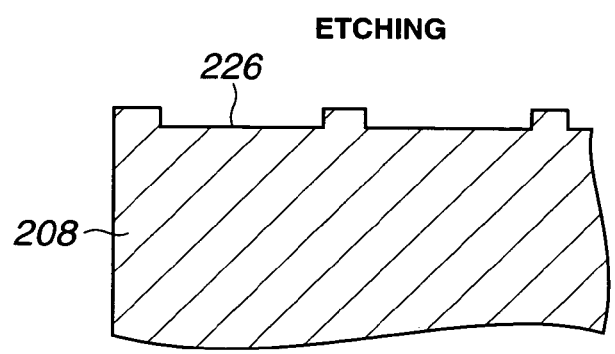
FIG. 25A is a cross-sectional view describing the manufacturing process at the rod side of the manufacturing method of the capacitive ultrasonic transducer in the ultrasonic probe tip portion.
Figure 25B:
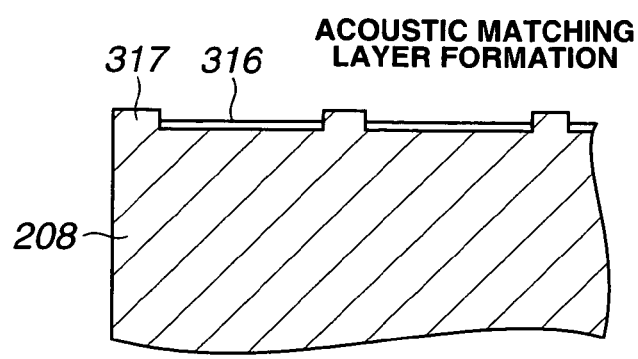
FIG. 25B is a cross-sectional view describing the manufacturing process at the rod side of the manufacturing method of the capacitive ultrasonic transducer in the ultrasonic probe tip portion.

The manufacturing method illustrated in FIG. 25A through FIG. 25J is a combination of the two manufacturing processes of a manufacturing process at the rod 208 side illustrated in FIG. 25A through FIG. 25C, and a manufacturing process at the capacitive ultrasonic transducer side illustrated in FIG. 25D through FIG. 25J.

With FIG. 25A through FIG. 25J, the manufacturing process at the rod 208 side proceeds in the sequence of FIG. 25A (etching of the rod bottom face), FIG. 25B (formation of the acoustic matching layer), and FIG. 25C (bonding as to the capacitive ultrasonic transducer).

Figure 25I:
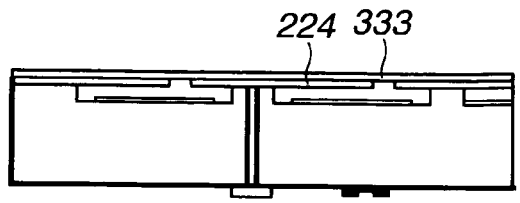
FIG. 25I is a cross-sectional view describing the manufacturing process at the transducer side of the manufacturing method of the capacitive ultrasonic transducer in the ultrasonic probe tip portion.
Figure 25J:
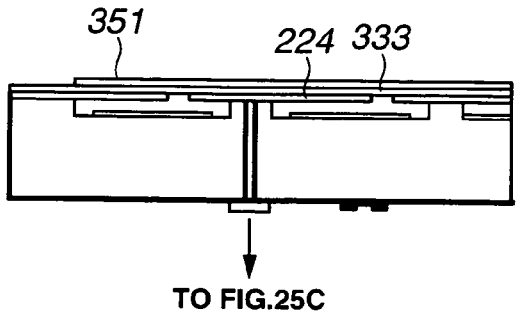
FIG. 25J is a cross-sectional view describing the manufacturing process at the transducer side of the manufacturing method of the capacitive ultrasonic transducer in the ultrasonic probe tip portion.

On the other hand, the manufacturing process at the capacitive ultrasonic transducer side proceeds in the sequence of FIG. 25D (etching of the silicon substrate, formation of the lower electrode), FIG. 25E (formation of the sacrifice layer), FIG. 25F (formation of the membrane layer), FIG. 25G (formation of the sacrifice layer removal hole), FIG. 25H (removal of the sacrifice layer), FIG. 25I (formation of the hole shielding film), and FIG. 25J (formation of the upper electrode).

With bonding as to the capacitive ultrasonic transducer in FIG. 25C in the manufacturing process at the rod 208 side, the silicon substrate 223 on which the capacitive ultrasonic transducer is formed following formation of the upper electrode in FIG. 25J in the manufacturing process at the capacitive ultrasonic transducer side is bonded to the rod 208 subjected to formation of the acoustic matching layer in FIG. 25B in the manufacturing process at the rod 208 side. Note that with the example in FIG. 25A through FIG. 25J, the positional relation between the signal electrode 225 and the ground electrode 351 illustrates the opposite configuration example in the case of FIG. 23 and FIG. 24.

Figure 26:
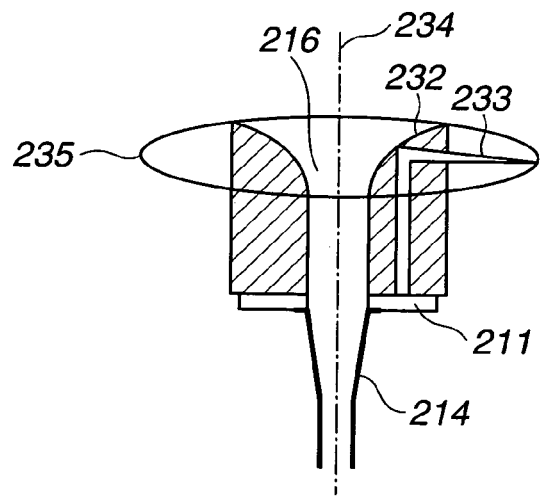
FIG. 26 is a diagram illustrating another example of the cross-sectional shape of the rod portion of an ultrasonic probe according to a third embodiment of the present invention.

FIG. 26 illustrates another example of the cross-sectional shape of the rod portion of an ultrasonic probe according to the third embodiment of the present invention. Reference numeral 232 denotes a coning curved face, 233 denotes a focusing ultrasonic beam, 234 denotes an ultrasonic beam rotation axis, and 235 denotes an ultrasonic beam rotation face.

The feature of the cross-sectional shape of the rod portion illustrated in FIG. 26 is in that a conical portion is not linear but rounded in shape. That is to say, the conical portion is formed in a trumpet-shaped curved face. Thus, upon forming a curved face, as illustrated in FIG. 16, the ultrasonic transducer and the rod serving as an ultrasonic propagation medium can focus an ultrasonic beam in the direction orthogonal to the insertion axis direction by lens effects due to a liquid acoustic binding medium in a state in which the ultrasonic transducer and the rod are stored within the sheath along with a liquid acoustic binding medium such as the water. That is to say, the coning curved face 232 is provided as focusing means.

Figure 27:
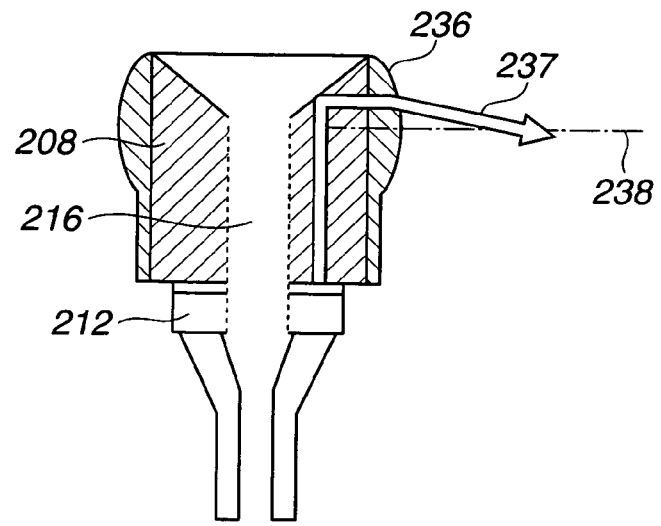
FIG. 27 is a diagram illustrating yet another example of the cross-sectional shape of the rod portion of an ultrasonic probe according to the third embodiment of the present invention.

FIG. 27 illustrates yet another example of the cross-sectional shape of the rod portion of the ultrasonic probe according to the third embodiment of the present invention. Reference numeral 236 denotes an acoustic lens, 237 denotes a focusing ultrasonic beam, and 238 denotes a lens central axis.

The feature of the cross-sectional shape of the rod portion illustrated in FIG. 27 is in that the acoustic lens 236 is provided on the outer circumference at the tip side of the rod 208 as means for focusing an ultrasonic beam.

Figure 28:
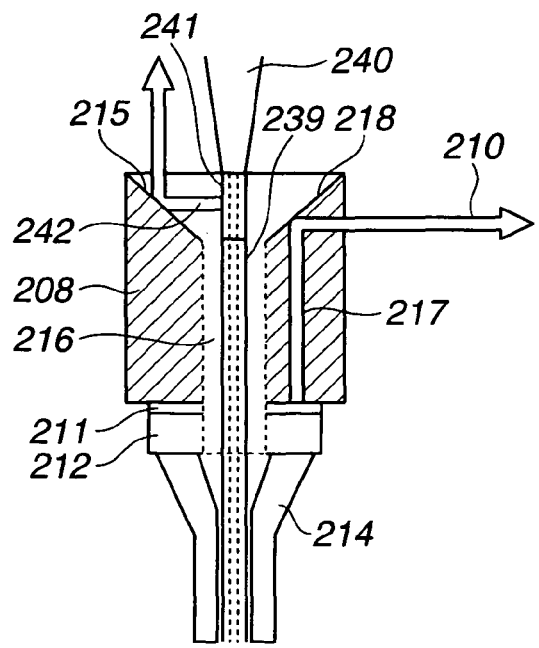
FIG. 28 is a cross-sectional view illustrating modification of the cross-sectional configuration of the rod portion of an ultrasonic probe according to the third embodiment of the present invention.
Figure 29:
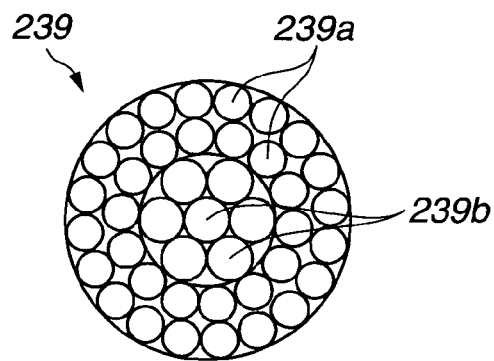
FIG. 29 is an enlarged cross-sectional view of the optical fiber in FIG. 28.

FIG. 28 illustrates a modification of the cross-sectional configuration of the rod portion of the ultrasonic probe according to the third embodiment of the present invention. FIG. 29 is an enlarged cross-sectional view of an optical fiber 239 in FIG. 28. With these drawings, reference numeral 239 denotes an optical fiber, 240 denotes light irradiation, 241 denotes an optical leakage processing portion, and 242 denotes diffusion light.

In FIG. 28, with the thick-walled cylindrical rod 208, the insertion axis portion is hollow, so for example, the optical fiber 239 is disposed in the inside diameter portion of the cylinder thereof, light is transmitted, or the light from a subject is received at the tip of the optical fiber 239, thereby observing an optical image. This is because in the event of an ultrasonic diagnostic system not employing an endoscope, there is the need to prepare for means for optically observing so as to serve as a substitute for an endoscope, which is different from the case of performing ultrasonic diagnosis within a body using the forceps hole of an endoscope.

The optical fiber 239 is a fiber bundle wherein multiple fibers are bundled such as illustrated in FIG. 29, but an arrangement is made wherein of the fiber bundle, several fibers at the outer circumferential side are employed as a light guide portion (portion for light radiation) 239a, and the residual several fibers at the center side are employed as a image guide portion (portion for optical image observation) 239b. That is to say, the fiber bundle is bundled in a concentric shape, the bundle 239a at the outer side emits light, and the bundle 239b at the inner side receives light, thereby performing observation.

The optical leakage processing portion 241 situated at the tip portion of the optical fiber 239 is formed with an outer face having a great number of irregularities (textured outer face) so as to diffuse light toward the outer circumference by the bundle outer circumferential portion, and is configured such that light is exuded to the outer circumferential face side from the light guide fiber. Accordingly, the optical fiber 239 can emit the diffusion light 242 not only forward as with the light irradiation 240, but also in the lateral direction generally orthogonal to the insertion axis, and reflect this at the outer face of the ultrasonic reflected face 215 of the rod 208 to irradiate this diffusely generally in the forward direction, though the light irradiation is emitted only forward.

Figure 30:
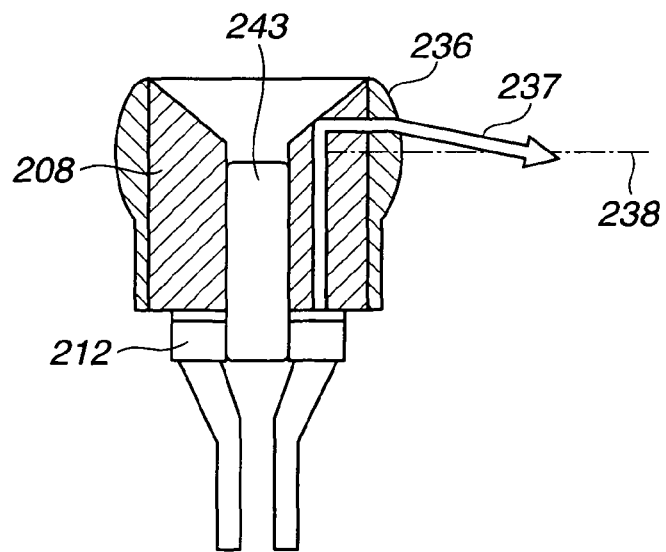
FIG. 30 is a cross-sectional view illustrating another modification of the cross-sectional configuration of the rod portion of an ultrasonic probe according to the third embodiment of the present invention.

FIG. 30 illustrates another modification of the cross-sectional configuration of the rod portion of the ultrasonic probe according to the third embodiment of the present invention. Reference numeral 236 denotes an acoustic lens, 237 denotes a focusing ultrasonic beam, 238 denotes a lens central axis, and 243 denotes a control circuit. That is to say, FIG. 30 illustrates a configuration wherein the control circuit 243 is added to the configuration in FIG. 27.

In FIG. 30, a configuration is provided wherein the control circuit 243 is disposed in the inside of the hollow hole 216 of the rod 208 on the cylinder. This effectively uses space, and also disposes the small-sized control circuit using IC technology. As for the control circuit 243, the control circuit of the ultrasonic transducer 211 and the like can be employed, and by being thus configured, a great number of signal processing circuits can be disposed nearby the ultrasonic transducer 211 in a bundle. As for a control circuit, there are various types of control circuit such as illustrated in FIG. 31 or FIG. 34.

Figure 31:
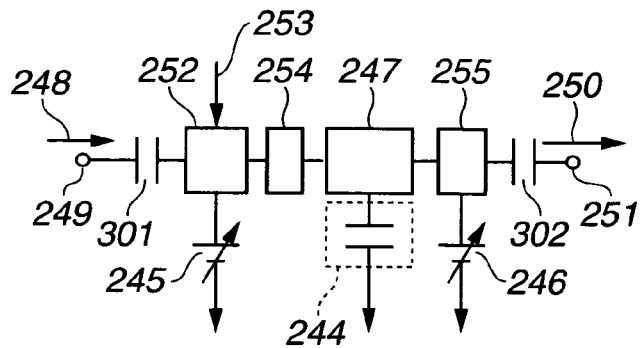
FIG. 31 is a block diagram of a two-way capacitive ultrasonic probe device according to the third embodiment of the present invention.

FIG. 31 illustrates a block diagram of a two-way capacitive ultrasonic probe device according to the third embodiment of the present invention. Also, FIG. 32 illustrates one example of the driving pulse signal waveform of the capacitive ultrasonic transducer element in FIG. 31.

With these drawings, reference numeral 244 denotes a capacitive ultrasonic transducer element, 245 and 246 denote DC bias power sources, 247 denotes a transmission/reception switchover switch, 248 denotes an RF pulse signal for transducer element driving, 249 denotes the input terminal of the RF pulse signal, 250 denotes a reception signal, 251 denotes the output terminal of the reception signal, 252 denotes an adder between the RF pulse signal and a DC bias signal, 253 denotes an addition command signal, 254 denotes a power amp, 255 denotes a charge amp, 301 and 302 denote DC prevention capacitors, 256 denotes a transducer element driving signal waveform, 257 denotes RF pulse signal components serving as a burst wave, trf denotes RF pulse signal duration, 258 denotes a DC bias signal, Vbias denotes DC bias voltage, tbias denotes DC bias signal duration, 260 denotes the leading-edge portion of the DC bias signal, and 261 denotes the trailing-edge portion of the DC bias signal, respectively.

In FIG. 31, a driving signal is input at the time of transmission and reception of an ultrasonic wave in increments of capacitive ultrasonic transducer element, thereby transmitting and receiving an ultrasonic wave, and basically, it is necessary to prepare for a driving signal wherein DC voltage, and RF voltage for outputting an ultrasonic wave are added.

Figure 32:
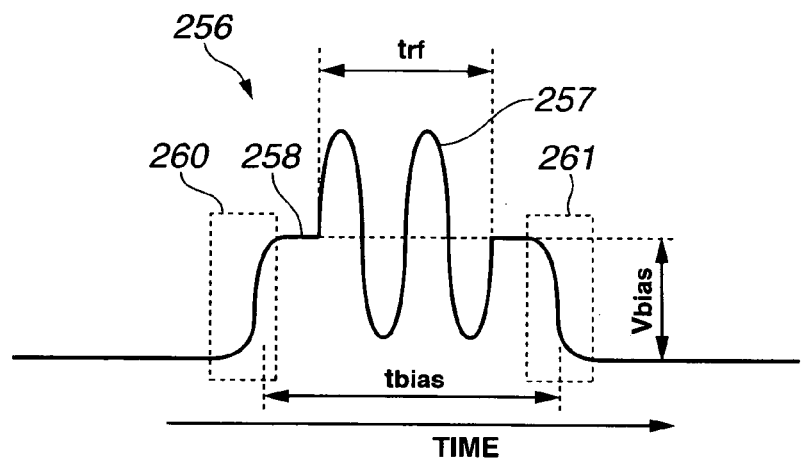
FIG. 32 is a waveform chart of an ultrasonic transducer driving pulse signal in which an RF pulse signal and a DC pulse signal are superimposed.

Following the RF pulse signal 248 being input to the input terminal 249, and DC components being removed at the DC prevention capacitor 301, upon the DC bias signal having a steady cycle from the DC bias power source 245 being added to the RF pulse signal 248 at the adder 252, a driving pulse signal such as illustrated in FIG. 32 can be obtained.

The RF pulse signal 248, and the DC bias signal from the DC bias power source 245 are low-voltage signals, the constant-voltage driving pulse signal following being added at the adder 252 is amplified at the power amp 254 to become a high-voltage driving pulse signal, and is applied to the capacitive ultrasonic transducer element 244 to drive the capacitive ultrasonic transducer element 244, thereby generating an ultrasonic wave.

The transmission/reception switchover switch 247 is a type of directional coupler, and in the event of transmitting an ultrasonic wave, the high-voltage driving pulse signal wherein the addition signal made up of the RF pulse signal input from the input terminal 249 and the DC bias signal is amplified is applied to the capacitive ultrasonic transducer element 244, thereby transmitting an ultrasonic wave, and in the event of receiving an ultrasonic wave, the capacitive ultrasonic transducer element 244 is switched over to reception use by switchover of the switch 247, the capacitive ultrasonic transducer element 244 receives an ultrasonic wave reflected at a diagnostic target, the echo signal from the capacitive ultrasonic transducer element 244 which received the ultrasonic wave is amplified at the charge amp 255, of which DC components are removed by the DC prevention capacitor 302, following which is output from the output terminal 251 as the reception signal 250.

The charge amp 255 includes three functions of a function wherein an electric charge signal is output as the output of the capacitive ultrasonic transducer element 244, so the charge thereof is received, and is converted into a voltage signal, a function for amplifying the voltage signal thereof so as to obtain high voltage, and a function wherein the output impedance of the capacitive ultrasonic transducer element 244 includes extremely high impedance, so the output of the capacitive ultrasonic transducer element 244 is converted into a low-impedance signal so as to match the circuit system of the subsequent stages. With regard to the impedance conversion function, the output terminal 251 is usually connected with a long cable of which impedance is low, e.g., 50 ohms. Accordingly, not matching with this low-impedance cable increases losses and reflection, and consequently, noise increases. Therefore, in order to prevent such losses and noise from occurrence, it is necessary to convert high impedance into low impedance in the vicinity of the transducer element as near as possible.

Figure 33:
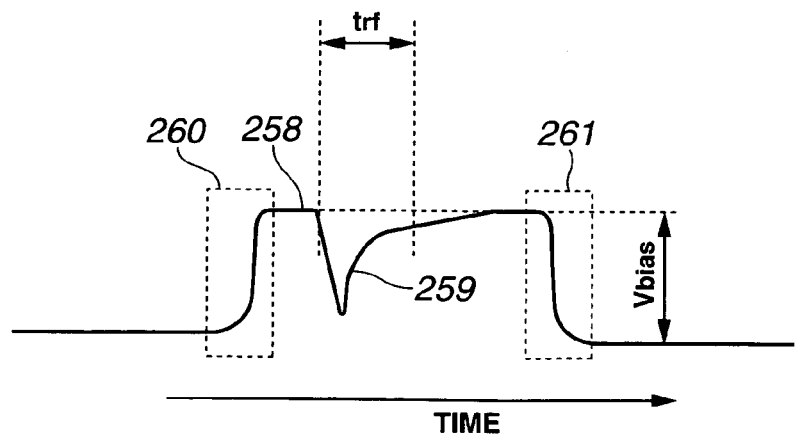
FIG. 33 is a diagram illustrating another waveform example of an ultrasonic transducer driving pulse signal.

Note that in FIG. 32, the leading-edge portion 260 and the trailing-edge portion 261 of the DC bias signal 258 are arranged so as to draw a smooth curve. This is because the DC bias signal to be actually applied to the capacitive ultrasonic transducer element 244 is high voltage, and in the event of the leading edge and trailing edge thereof being steep, deterioration of the capacitive ultrasonic transducer element 244 is accelerated, so the above arrangement is made for preventing this situation. In FIG. 32, the RF pulse signal 257 to be added to the DC bias signal 258 forms a burst wave, but as for the RF pulse signal, a spike wave 259 such as illustrated in FIG. 33 may be employed. In the event of employing the spike wave such as illustrated in FIG. 33 as well, the amplitude property and frequency distribution property, i.e., spectrum property can be obtained regarding the echo signal to be received by adjusting DC bias voltage Vbias.

FIG. 34 illustrates a block diagram of a capacitive ultrasonic probe device configured of a two-way capacitive ultrasonic transducer array. Note that FIG. 34 illustrates a configuration wherein the DC bias power source at the reception side is eliminated. This is because as a result of the present applicant performing an experiment regarding a capacitive ultrasonic transducer, confirmation is made that an ultrasonic wave reflected at a diagnostic target can be normally received even without the DC bias voltage supplied by the DC bias power source for reception at the time of reception.

In FIG. 34, reference numeral 470 denotes a capacitive ultrasonic probe device. Reference numeral 427 denotes a capacitive ultrasonic transducer array made up of multiple two-way-type capacitive ultrasonic transducer elements 425 being arrayed. With regard to each of the capacitive ultrasonic transducer elements 425, the terminal at one side is grounded to ground 443, and the terminal at the other side is connected to the transducer terminal a of each of transmission/reception switchover circuits 436 making up a transmission/reception changeover switch array 426. The transmission/reception switchover circuit 436 comprises a transducer terminal a to be connected to a capacitive ultrasonic transducer element 425, a transmission side terminal b to be connected to a transmission side circuit, and a reception side terminal c to be connected to a reception side circuit.

The capacitive ultrasonic transducer elements 425 are radial scan-type array-type transducers for scanning an ultrasonic beam around the insertion axis within a body cavity, for example. With the multiple transmission/reception switchover circuits 436 making up the transmission/reception switchover switch array 426, transmission/reception is switched with a transmission/reception control signal 439.

Reference numeral 428 denotes a transmission sequential switchover switch, 429 denotes a driving circuit array made up of multiple driving signal generators being arrayed, 430 denotes a transmission DC bias generating circuit serving as means for supplying DC bias voltage, and 431 denotes a RF pulse generating circuit.

The RF pulse generating circuit 431 includes a function for generating an RF pulse signal having 10 V or lower amplitude level. This RF pulse signal of which frequency is 1 kHz through 10 kHz is generated with information of frequency, pulse width, and repeat time under control of the control circuit 473 made up of a microprocessor and so forth.

The transmission sequential switchover switch 428 includes a function for sequentially selecting channels corresponding to the multiple capacitive ultrasonic transducer elements 425 making up the capacitive ultrasonic transducer array 427 one by one. That is to say, the transmission sequential switchover switch 428 inputs the RF pulse signal from the RF pulse generating circuit 431, sequentially determines a switchover timing under control of the control circuit 473, and sequentially performs switchover at a high speed. The transmission sequential switchover switch 428 includes a function for switching over the channels one by one in regular order according to a switch changeover procedure such as a, b, c, and so on through n, a, b, c, and so on through n. Then, the transmission sequential switchover switch 428 outputs the RF pulse signal to the respective channels corresponding to the respective transducer elements.

The DC bias generating circuit 430 has a function for generating a DC pulse signal having a predetermined pulse width including a low voltage level of 10 V or less for each steady cycle. The DC bias generating circuit 430 generates a DC bias signal, i.e., a DC pulse signal in sync with the switchover timing of each of the RF pulse signals to be output from the transmission sequential switchover switch 428 under control of the control circuit 473, and supplies this to the driving circuit array 429. That is to say, unshown multiple output lines are output from the DC bias generating circuit 430, corresponding to multiple driving signal generating circuits corresponding to the number of transducer elements making up the driving circuit array 429, DC pulse signals matching with the switchover timing of transmission RF pulse signals are sequentially generated, and are sequentially supplied to the multiple driving signal generating circuits.

The driving circuit array 429 is made up of multiple driving signal generating circuits, each of the driving signal generating circuits adds a low-voltage DC pulse signal having delay corresponding to each of the channels from the DC bias generating circuit 430, and a low-voltage RF pulse signal to be output from each of the switch circuits of the transmission sequential switchover switch 428 to generate a low-voltage driving pulse signal, following which amplifies the driving pulse signal to generate a driving pulse signal for driving a high-voltage ultrasonic transducer element of 150 V through 200 V, and supplies this to the transmission side terminal b of each of the transmission/reception switchover circuits 436 of the transmission/reception switchover switch array 426.

Each of the transmission/reception switchover circuits 436 of the transmission/reception switchover switch array 426 comprises a transmission side terminal b for inputting the driving pulse signal from each of the driving signal generating circuits of the driving circuit array 429 at the time of transmission, a reception side terminal c for outputting the pulse echo signal from each of the capacitive ultrasonic transducer elements 425 of the capacitive ultrasonic transducer array 427 at the time of reception, and a common terminal a for performing input or output of a signal corresponding to each of the capacitive ultrasonic transducer elements 425 of the capacitive ultrasonic transducer array 427 when switching over to the transmission side terminal b or reception side terminal c at the time of transmission or reception.

The multiple transmission/reception switchover circuits 436 making up the transmission/reception switchover switch array 426 correspond to the multiple capacitive ultrasonic transducer elements 425 making up the capacitive ultrasonic transducer array 427 one on one. When each of the multiple transmission/reception switchover circuits 436 obtains its transmission timing, the above high-voltage driving pulse signal for ultrasonic transducer element driving is transmitted to the capacitive ultrasonic transducer element corresponding to each of the multiple transmission/reception switchover circuits 436 to generate an ultrasonic wave.

An echo signal is returned from organism tissue in response to the ultrasonic wave transmitted from each of the capacitive ultrasonic transducer elements 425 of the capacitive ultrasonic transducer array 427. The echo signal thereof is received at each of the capacitive ultrasonic transducer elements 425 of the capacitive ultrasonic transducer array 427 in accordance with receiving timing, and is transmitted to each of the charge amps making up a charge amp array 432 for pre-amplification.

The charge amp array 432 includes an impedance conversion function for performing impedance matching between the high-impedance capacitive ultrasonic transducer elements 425 serving as the previous stage of the charge amp and a low-impedance circuit system serving as the subsequent stage of the charge amp, and an amplification function for voltage-amplifying the minute signal from the capacitive ultrasonic transducer elements 425. That is to say, the capacitive ultrasonic transducer elements 425 include extremely high output impedance, so the transducer element echo output signal thereof is transmitted to the respective charge amps of the charge amp array 432 which operates as a high-input-impedance preamp for amplification. Also, the ultrasonic signal which returns as an echo signal is extremely weak, and also in the event of the output echo signal from the capacitive ultrasonic transducer elements 425 being converted into voltage, the value of the voltage thereof is extremely small such as 0.5 V through 0.005 V or so, and accordingly, it is necessary for the charge amp array 432 to voltage-amplify this signal up to 100 through 1000 times for example.

The output signal of the charge amp array 432 is transmitted to a filter array 433, where various types of noise components including RF noise are removed, following which the output signal is transmitted to an A/D converter 434 to be converted into a digital signal, and is transmitted to a reception sequential switchover switch 435 of the second stage. The reception sequential switchover switch 435 is made up of a switch which is sequentially switched over one by one at a steady speed.

In FIG. 34, the capacitive ultrasonic transducer array 427 in which the multiple capacitive ultrasonic transducer elements 425 are arrayed is employed, so an individual echo signal can be received at the many capacitive ultrasonic transducer elements 425, but the reception sequential switchover switch 435 is employed for gathering the many received echo signals together.

The reception sequential switchover switch 435 includes a function for sequentially selecting the channels corresponding to the multiple capacitive ultrasonic transducer elements 425 making up the capacitive ultrasonic transducer array 427 one by one. That is to say, the reception sequential switchover switch 435 inputs the digital signal from the A/D converter 434, determines sequential switchover timing under control of the above control circuit 473, and sequentially performs switchover at a high speed. The reception sequential switchover switch 435 includes a function for switching over the channels one by one in regular order according to a switch changeover procedure such as a, b, c, and so on through n, a, b, c, and so on through n. The echo signal from the respective channels corresponding to the respective transducer elements can be received by this switchover timing.

A reception signal 442 obtained by sequential switchover of the reception sequential switchover switch 435 is input to a phase inversion synthetic circuit 477 serving as a harmonic wave signal processing circuit. The phase inversion synthetic circuit 477 extracts a second harmonic wave signal within a reception signal using second harmonic wave extraction technology described later with FIG. 36, and generates a signal for harmonic imaging diagnosis.

Note that the ultrasonic pulse signal which the capacitive ultrasonic transducer element 425 transmits to organism tissue is a signal made up of the fundamental wave of a frequency fO, but when the fundamental wave fO propagates organism tissue, a harmonic wave is generated by the nonlinearity of the organism tissue. This harmonic wave enters the inside of an echo signal serving as a reflection signal, returns, and is received at the capacitive ultrasonic transducer element 425. Of the echo signal to be reflected, the second harmonic wave signal is extracted at the phase inversion synthetic circuit 477.

With a digital scan converter (abbreviated as DSC in the drawing) 478, a signal for harmonic imaging diagnosis is employed and converted into a picture signal to display this on the monitor 479, whereby ultrasonic diagnosis can be performed.

The control circuit 473 performs RF pulse generating control of the RF pulse generating circuit 431, delay control of the DC bias generating circuit 430, sequential switchover switch 428, and reception sequential switchover switch 435, and control of the driving circuit array 429, charge amp array 432, filter array 433, phase inversion synthetic circuit 477, and digital scan converter 478, and in addition to these, performs selection control of a transmission transducer element and a reception transducer element in the multiple transmission/reception switchover circuits 436 making up the transmission/reception switchover switch array 426 by using the transmission/reception switchover control signal 439.

Next, description will be made regarding operation of the capacitive ultrasonic transducer array in FIG. 34 with reference to FIG. 35.

The top of FIG. 35 illustrates the waveform of the control pulse signal 445 to be generated at the control circuit 473 for controlling the driving circuit array 429. The bottom of FIG. 35 illustrates the waveform of the ultrasonic transducer element driving pulse signal 446 (this reference numeral 446 is not shown) in a low-voltage state, which is generated within each of the driving signal generating circuits of the driving circuit array 429.

Under control of the control pulse signal 445 in the top of FIG. 35, each of the driving signal generating circuits of the driving circuit array 429 adds the low-voltage RF pulse signal to be obtained by sequential switchover of the sequential switchover switch 428 and the low-voltage DC pulse signal matching with the RF pulse signal from the DC bias generating circuit 430 to generate the low-voltage driving pulse signal 446 illustrated in the bottom of FIG. 35, following which amplifies the driving pulse signal 446 to generate a high-voltage driving pulse signal 447 for ultrasonic transducer element driving, and supplies this to the transmission side terminal b of each of the transmission/reception switchover circuit 436 of the transmission/reception switchover switch array 426.

In the top of FIG. 35, reference numeral 581 denotes a +DC bias activating timing pulse, 582 denotes an RF signal generating timing pulse, 583 denotes a +DC bias stopping timing pulse, 584 denotes a −DC bias activating timing pulse, 585 denotes an RF signal generating timing pulse, 586 denotes a −DC bias stopping timing pulse, Vrf denotes RF pulse signal voltage for specifying RF pulse signal generating duration trf, Vdc+ denotes +DC bias activating/stopping pulse voltage, and Vdc- denotes –DC bias activating/stopping voltage, respectively.

In the bottom of FIG. 35, reference numeral 451 denotes a +DC pulse signal, 452 denotes a –DC pulse signal, 461 and 462 denote RF signals, trf denotes RF pulse signal generating duration, tbias denotes DC bias signal generating duration, Vdc+ denotes +DC bias activating/stopping pulse voltage, Vdc– denotes –DC bias activating/stopping pulse voltage, Vbias+ denotes +DC bias voltage, and Vbias-denotes –DC bias voltage, respectively.

The pulse width trf of the positive voltage pulses 582 and 585 in the control pulse signal 445 illustrated in the top of FIG. 35 is for specifying duration wherein the RF pulse signals 461 and 462 in the bottom of FIG. 35 are output. The negative voltage pulses 581 and 583 in the top of FIG. 35 specify the timing of start and stop of application of positive DC bias voltage Vbias+ in the bottom of FIG. 35, the negative voltage pulses 584 and 586 in the top of FIG. 35 specify the timing of start and stop of application of negative DC bias voltage Vbias– in the bottom of FIG. 35, and these negative voltage pulses 581, 583, 584, and 586 have the opposite pulse polarity of the pulses 582 and 585 corresponding to the RF signal output duration. Also, the difference of magnitude of voltage values (Vdc+ and Vdc–) in the top of FIG. 35 specifies the difference of polarity of the DC bias voltage Vbias+ and Vbias– illustrated in the bottom of FIG. 35.

Upon driving the ultrasonic transducer element 425 based on the signal waveforms in the bottom of FIG. 35, an ultrasonic wave having an inversed phase is transmitted. Upon viewing the first peak of the pulses, the preceding pulse has Vbias++Vop (=the maximum value of amplitude), and the subsequent pulse has Vbias–+Vop (=the minimum value of amplitude), and accordingly, the phases of both are inverted. However, Vop represents the amplitude of RF pulse signals 61 and 62.

The respective driving signal generating circuits of the driving circuit array 429 include a function for generating the driving pulse signal 446 in which the RF pulse signals 461 and 462 are superimposed on the DC pulse signals 451 and 452 respectively, a first superimposed pulse signal in which the RF pulse signal 461 is superimposed on the DC pulse signal 451 of one polarity, e.g., a positive polarity, and a second superimposed pulse signal in which the opposite polarity of the DC pulse signal employed at the time of forming the first superimposed pulse signal, e.g., the RF pulse signal 462 of the same type (amplitude, frequency, and polarity) as the RF pulse signal 461 employed at the time of forming the first superimposed pulse signal, are combined so as to continue in a predetermined time interval to generate a double pulse signal, thereby generating the low-voltage ultrasonic transducer element driving pulse signal 446 such as illustrated in the bottom of FIG. 35.

Upon the high-voltage signal 447 obtained by amplifying the ultrasonic transducer element driving pulse signal 446 having a double pulse signal waveform being applied to the respective capacitive ultrasonic transducer elements 425 via the respective transmission/reception switchover circuits 436 from the respective driving signal generating circuits of the driving circuit array 429, of the ultrasonic signals to be output from the respective capacitive ultrasonic transducer elements 425, the relation between the ultrasonic signal corresponding to the first RF pulse signal of the above double pulse signal and the ultrasonic signal corresponding to the next RF pulse signal becomes a relation wherein the phases of both are reversed such as illustrated in the pulses A and B in FIG. 14A in the event of illustrating this relation using two wave numbers in a modeled manner. Subsequently, upon transmitting the double pulse signal in which such phase-inverted pulses are combined to organism tissue, a harmonic wave is super imposed on the fundamental ultrasonic wave by influence of the nonlinearity of the organism tissue. In this case, the response of the fundamental wave is primary, i.e., the first root, and the response of the second harmonic wave is the square root. The term "square root" means that negative components become positive. The fundamental wave is the first root, so positive remains as positive, and negative remains as negative. Accordingly, the fundamental wave components of an ultrasonic signal to be received at the respective capacitive ultrasonic transducer elements 425 are the same as those of the transmission ultrasonic signal in FIG. 14A as illustrated in the top of FIG. 14B, but the second harmonic wave components of a receiving ultrasonic signal become positive components alone such as illustrated in the bottom of FIG. 14B.

Therefore, with the circuit system at the reception side, upon adding the pulse A and the pulse B making up the double pulse in a reception ultrasonic signal when assuming that the time difference td of the pulses A and B is zero, the fundamental wave components are eliminated by adding the positive components and the negative components, and the second harmonic wave components are doubled by adding the positive components and the positive components. That is to say, only the second harmonic wave components can be extracted. This is the harmonic wave components extraction technology of the harmonic imaging technology with capacitive ultrasonic transducers. According to such harmonic wave components extraction technology, harmonic wave components having small acoustic pressure of 10 through 20 dB as compared with the acoustic pressure of the fundamental wave components can be separated and extracted from a reception signal in which the fundamental wave components and the harmonic wave components are mixed.

For example, with the above phase inversion synthetic circuit 477, as means for setting the time difference td to zero, the first pulse A is temporarily stored in the memory, and the stored first pulse A and the pulse B are added at the point of the subsequent pulse B arriving. Thus, the double pulse in which a pair of pulses of which phase is reversed are combined is applied to organism tissue, the response of the fundamental wave (strictly, all of odd-ordered) is primary, i.e., the first root, and the response of the second harmonic wave (strictly, all of even-ordered) eliminates a negative signal, and accordingly, upon adding both pulses while aligning both phases, the fundamental wave (strictly, all of odd-ordered) components are eliminated, and the second harmonic wave (strictly, all of even-ordered) alone remains.

Note that with the actual ultrasonic diagnosis, it is necessary to observe the fundamental wave as well as a harmonic wave. The fundamental wave is extracted with another means which have been employed conventionally. Consequently, the extracted images of both are added to generate an ultrasonic image.

Incidentally, with the DC pulse signal serving as DC bias voltage of the ultrasonic transducer element driving pulse signal illustrated in the bottom of FIG. 35, the leading edge and trailing edge of the pulse thereof are almost perpendicular. Thus, upon applying steeply high DC bias voltage (100 V or so) to an ultrasonic transducer intermittently, a capacitive ultrasonic transducer is readily deteriorated, which may shorten the life as a transducer. Therefore, an arrangement may be made wherein with the leading edge portion and the trailing edge portion of the DC pulse signals 451 and 452 as well, as illustrated in FIG. 32, the leading edge portion and the trailing edge portion thereof are blunted so as to become a smooth slope, thereby preventing high voltage from being applied to an ultrasonic transducer steeply.

The above third embodiment of the present invention can realize a capacitive ultrasonic probe device which can be used within a body cavity using a capacitive ultrasonic transducer with operating effective voltage being suppressed low, and also can be used for harmonic imaging diagnosis.

It is needless to say that the present invention can be applied to a capacitive ultrasonic probe device, an ultrasonic diagnostic device employing this, and also an ultrasonic endoscope diagnostic device which enables an endoscope image and an ultrasonic image to be obtained simultaneously by combing an electronic endoscope device and an ultrasonic diagnostic device.

What is claimed is:

1. A capacitive ultrasonic probe device having a configuration wherein each of multiple ultrasonic transducer units is formed with multiple ultrasonic transducer elements in increments of driving, which are formed by disposing multiple capacitive ultrasonic transducer cells using a common electrode along a generally cylindrical shaped outer side face provided at the tip side of an insertion portion capable of being inserted into a body cavity, being arrayed in the direction in parallel with the center axis of the generally cylindrical shape as division increments, and the multiple ultrasonic transducer units are arrayed along the outer circumference of the generally cylindrical shape in a direction orthogonal to a longitudinal direction of the multiple ultrasonic transducer units.

2. The capacitive ultrasonic probe device according to claim 1, wherein the multiple ultrasonic transducer units are joined to a flexible circuit substrate formed in a generally cylindrical shape.

3. The capacitive ultrasonic probe device according to claim 2, wherein control circuit means for individually controlling the ultrasonic transducer elements are disposed in the inside of the flexible circuit substrate formed in a generally cylindrical shape.

4. The capacitive ultrasonic probe device according to claim 3, wherein the control circuit means are made up of multiple divided control circuit units, and also the respective control circuit units are disposed at the inner circumferential face side facing the ultrasonic transducer units.

5. The capacitive ultrasonic probe device according to claim 4, wherein the control circuit units are divided into multiple control circuit elements, and each of the control circuit elements includes:
driving means for applying a driving signal to the ultrasonic transducer element at each facing position; and
reception means for performing reception processing as to a reception signal.

6. The capacitive ultrasonic probe device according to claim 4, wherein a switching circuit for switching a set of the multiple ultrasonic transducer units and the control circuit unit is provided in the inside of the flexible circuit substrate.

7. The capacitive ultrasonic probe device according to claim 4, wherein a thermal conductive resin is filled in a gap between the driving control units disposed in the cylindrical shaped inner side.

8. The capacitive ultrasonic probe device according to claim 1, further comprising:
scanning means for applying a driving signal to the multiple ultrasonic transducer elements within each of the multiple ultrasonic transducer units with a phase difference, and performing ultrasonic beam scanning.

9. The capacitive ultrasonic probe device according to claim 8, wherein control of the phase difference is performed by external control means, and is performed via a signal cable and the switching circuit.

10. The capacitive ultrasonic probe device according to claim 1, wherein externally applying a driving signal enables ultrasonic beam scanning by the multiple ultrasonic transducer elements within each of the multiple ultrasonic transducer units to be sector-scanned.

11. The capacitive ultrasonic probe device according to claim 1, wherein externally applying a driving signal enables radial scanning by sequentially switching scanning of the multiple ultrasonic transducer units.

12. The capacitive ultrasonic probe device according to claim 1, further comprising:
driving signal generating means for generating a driving signal to be applied to the ultrasonic transducer elements,
wherein the driving signal generating means generates a driving signal in which a DC-bias signal is superimposed on an RF signal.

13. The capacitive ultrasonic probe device according to claim 12, wherein the DC-bias signal to be superimposed on the RF signal is a DC pulse signal.

14. The capacitive ultrasonic probe device according to claim 1, further comprising:
driving signal generating means for generating a driving signal to be applied to the ultrasonic transducer elements,
wherein the driving signal generating means inputs a low-voltage pulse, and outputs a high-voltage RF pulse signal.

15. The capacitive ultrasonic probe device according to claim 1, further comprising:
driving signal generating means for generating a driving signal to be applied to the ultrasonic transducer elements,
wherein the driving signal generating means inputs a low-voltage pulse, and outputs a high-voltage RF pulse signal on which DC-bias voltage is superimposed.

16. The capacitive ultrasonic probe device according to claim 1, further comprising:
driving signal generating means for generating a driving signal to be applied to the ultrasonic transducer elements,
wherein the driving signal generating means inputs a low-voltage pulse, and outputs double pulses in which a high-voltage RF pulse signal on which positive DC-bias voltage is superimposed, and a high-voltage RF pulse signal on which negative DC-bias voltage is superimposed are combined.

17. The capacitive ultrasonic probe device according to claim 16, further comprising:
means for temporarily storing an ultrasonic response signal to be previously generated regarding a reception ultrasonic signal obtained by driving control and coupled, and superimposing both signals at the time of a subsequent ultrasonic response signal occurring.

18. The capacitive ultrasonic probe device according to claim 1, wherein the tip side of the insertion portion comprising:
multiple coaxial cables;
a cylindrical sheath which excels in ultrasonic transmittance, and is disposed so as to accommodate the coaxial cables; and
acoustic binding solution which is filled in between multiple ultrasonic transducers arrayed on the cylindrical outer side face and the cylindrical shaped sheath.

19. The capacitive ultrasonic probe device according to claim 18, wherein the cylindrical shaped sheath which excels in ultrasonic transmittance can be balloon-deformed by the pressure of the acoustic binding solution.

20. A capacitive ultrasonic probe device for inserting an ultrasonic probe into a body cavity, and performing ultrasonic diagnosis within a body by rotating and scanning an ultrasonic beam around the insertion axis, comprising:
  an ultrasonic transducer disposed and configured such that the ultrasonic probe emits an ultrasonic wave in the insertion-axis direction; and
  an ultrasonic propagation medium having a configuration including angular components for reflecting an ultrasonic wave emitted and propagated in the insertion-axis direction from the ultrasonic transducer in a predetermined angular direction as to the insertion axis.

21. The capacitive ultrasonic probe device according to claim 20, wherein the ultrasonic transducer and the ultrasonic propagation medium are stored in the sheath along with a fluid acoustic binding medium.

22. The capacitive ultrasonic probe device according to claim 20, wherein the ultrasonic transducer has a ring shape, and the ultrasonic propagation medium has a cylindrical shape of which the diameter thickness is great, which are disposed and bonded such that both inside diameter circles are concentrically situated.

23. The capacitive ultrasonic probe device according to claim 22, wherein the ultrasonic transducer is a piezoelectric transducer.

24. The capacitive ultrasonic probe device according to claim 22, wherein the ultrasonic transducer is a capacitive ultrasonic transducer.

25. The capacitive ultrasonic probe device according to claim 24, wherein the capacitive ultrasonic transducer includes means for controlling ultrasonic transmission/reception with a capacitive ultrasonic transducer element made up of multiple capacitive ultrasonic transducer cells radially disposed as a unit.

26. The capacitive ultrasonic probe device according to claim 25, further comprising:
  control means having a configuration wherein the multiple capacitive ultrasonic transducer elements are arrayed in the direction along the circumference of the ultrasonic propagation medium with the longitudinal direction thereof being disposed in the diameter direction, and scanning an ultrasonic wave in the radial direction by sequentially changing a switch.

27. The capacitive ultrasonic probe device according to claim 25, wherein the capacitive ultrasonic transducer cells are made up of a hollow portion formed on the silicon substrate, a membrane formed within the hollow portion so as to divide the hollow portion, a first electrode mounted on the membrane, a second membrane disposed so as to fill in the hollow portion, and a second electrode formed on the second membrane.

28. The capacitive ultrasonic probe device according to claim 27, wherein the second electrode is a grounding electrode, and the first electrode is an electrode for signal input/output.

29. The capacitive ultrasonic probe device according to claim 25, wherein the means for performing control so as to transmit/receive an ultrasonic wave with the capacitive ultrasonic transducer element as a unit comprising:
  a transmission/reception switchover switch;
  pulser means for applying a driving signal to the capacitive ultrasonic transducer element;
  charge amp means for processing a reception signal; and
  selecting circuit means for selecting the capacitive ultrasonic transducer elements sequentially or by group.

30. The capacitive ultrasonic probe device according to claim 29, wherein the pulser means include means for outputting a signal in which a high-frequency pulse signal and a DC pulse signal are superimposed.

31. The capacitive ultrasonic probe device according to claim 30, wherein the high-frequency pulse signal is either of a spike wave or burst wave.

32. The capacitive ultrasonic probe device according to claim 30, wherein the DC pulse signal draws a smooth curve at the leading edge portion and trailing edge portion thereof.

33. The capacitive ultrasonic probe device according to claim 30, further comprising:
  means for repeatedly applying a signal made up of a pair of a signal superimposed with the positive phase of the DC pulse signal, and a signal superimposed with the negative phase of the DC pulse signal.

34. The capacitive ultrasonic probe device according to claim 22, wherein the thick-walled cylindrical shaped ultrasonic propagation medium has a configuration at the inside diameter hollow portion thereof so as to insert an optical fiber, and irradiate or enter light from the tip of the optical fiber.

35. The capacitive ultrasonic probe device according to claim 22, wherein the thick-walled cylindrical shaped ultrasonic propagation medium makes up a part of a control circuit at the inside diameter hollow portion thereof.

36. The capacitive ultrasonic probe device according to claim 20, wherein the ultrasonic propagation medium is made up of an inorganic low-loss solid material.

37. The capacitive ultrasonic probe device according to claim 36, wherein the inorganic low-loss solid material is any one of sapphire, silicon monocrystal, quartz glass, crystal, high-density alumina ceramics, and zirconia ceramics.

38. The capacitive ultrasonic probe device according to claim 20, wherein the ultrasonic propagation medium is made up of a polymer low-loss solid material.

39. The capacitive ultrasonic probe device according to claim 38, wherein the polymer low-loss solid material is any one of a polystyrene resin, acrylic resin, polyurethane resin, phenol resin, and polyetherimide.

40. The capacitive ultrasonic probe device according to claim 20, wherein the predetermined angular direction is 90 degrees as to the insertion axis.

41. The capacitive ultrasonic probe device according to claim 20, wherein at the tip portion of the ultrasonic propagation medium, means for reflecting an ultrasonic wave in a predetermined angular direction makes up a face in a conical shape.

42. The capacitive ultrasonic probe device according to claim 41, wherein the face in a conical shape includes a curved face.

43. The capacitive ultrasonic probe device according to claim 20, wherein the ultrasonic propagation medium includes a fluid acoustic binding medium on the outer side face in the vicinity where an ultrasonic wave is emitted, and also includes an acoustic matching layer made up of at least one layer for subjecting the fluid acoustic binding medium and the ultrasonic propagation medium to acoustic matching on the outer side face in the vicinity where an ultrasonic wave is entered.

44. The capacitive ultrasonic probe device according to claim 20, wherein the ultrasonic propagation medium includes an acoustic lens on the outer side face in the vicinity where an ultrasonic wave is emitted.

* * * * *